US012805753B2

(12) United States Patent
Guerrero et al.

(10) Patent No.: US 12,805,753 B2
(45) Date of Patent: Nov. 24, 2026

(54) FITNESS TRAINING SYSTEM FOR MERGING ENERGY EXPENDITURE CALCULATIONS FROM MULTIPLE DEVICES

(71) Applicant: NIKE, Inc., Beaverton, OR (US)

(72) Inventors: Adriana Guerrero, Portland, OR (US); Steven H. Walker, Camas, WA (US); Aaron B. Weast, Portland, OR (US)

(73) Assignee: NIKE, Inc., Beaverton, OR (US)

( * ) Notice: Subject to any disclaimer, the term of this patent is extended or adjusted under 35 U.S.C. 154(b) by 183 days.

(21) Appl. No.: 18/768,355

(22) Filed: Jul. 10, 2024

(65) Prior Publication Data

US 2024/0358278 A1 Oct. 31, 2024

Related U.S. Application Data

(63) Continuation of application No. 18/157,290, filed on Jan. 20, 2023, now Pat. No. 12,064,232, which is a (Continued)

(51) Int. Cl.
*A61B 5/11* (2006.01)
*A61B 5/00* (2006.01)
(Continued)

(52) U.S. Cl.
CPC .............. *A61B 5/11* (2013.01); *A61B 5/0004* (2013.01); *A61B 5/002* (2013.01); *A61B 5/4866* (2013.01); *A61B 5/744* (2013.01); *A63B 24/0003* (2013.01); *A63B 24/0006* (2013.01); *A63B 24/0062* (2013.01); *A63F 13/5375* (2014.09); *A63F 13/822* (2014.09); *G16Z 99/00* (2019.02); *A63B 2024/0012* (2013.01);
(Continued)

(58) Field of Classification Search
CPC ... A61B 5/11; A61B 5/4866; A63B 2230/755; A63B 24/0003; A63B 24/0006; A63B 24/0062; A63B 2230/75
See application file for complete search history.

(56) References Cited

U.S. PATENT DOCUMENTS

| | | | |
|---|---|---|---|
| 3,145,484 A | 8/1964 | Bayley | |
| 3,845,484 A | 10/1974 | Sawicki et al. | |

(Continued)

FOREIGN PATENT DOCUMENTS

| | | | | |
|---|---|---|---|---|
| CN | 2905028 Y | | 5/2007 | |
| CN | 105849672 A | * | 8/2016 | ........... A61B 5/1123 |

(Continued)

OTHER PUBLICATIONS

Jun. 3, 2015—(WO) ISR & WO—App. No. PCT/US14/060366.
(Continued)

*Primary Examiner* — Steven J Hylinski
(74) *Attorney, Agent, or Firm* — Banner & Witcoff, Ltd.

(57) ABSTRACT

Systems and methods for prompting a user to perform an exercise and monitoring the exercise are provided. Multiple independent sensors or sensor systems may be used to calculate energy expenditure. Various criteria may be used to manually or automatically select the independent sensor or sensor system or combination that will be used with the energy expenditure calculations.

20 Claims, 18 Drawing Sheets

Related U.S. Application Data continuation of application No. 17/352,932, filed on Jun. 21, 2021, now Pat. No. 11,564,597, which is a continuation of application No. 16/199,874, filed on Nov. 26, 2018, now Pat. No. 11,045,114, which is a continuation of application No. 14/513,540, filed on Oct. 14, 2014, now Pat. No. 10,136,840.

(60) Provisional application No. 61/890,672, filed on Oct. 14, 2013.

(51) Int. Cl.
*A63B 24/00* (2006.01)
*A63F 13/5375* (2014.01)
*A63F 13/822* (2014.01)
*G16Z 99/00* (2019.01)

(52) U.S. Cl.
CPC ... *A63B 2024/0065* (2013.01); *A63B 2230/75* (2013.01); *A63B 2230/755* (2013.01); *A63F 2300/305* (2013.01); *A63F 2300/807* (2013.01)

(56) References Cited

U.S. PATENT DOCUMENTS

| | | | |
|---|---|---|---|
| 4,192,000 | A | 3/1980 | Lipsey |
| 4,578,769 | A | 3/1986 | Frederick |
| 4,696,051 | A | 9/1987 | Breeden |
| 4,813,436 | A | 3/1989 | Au |
| 5,184,295 | A | 2/1993 | Mann |
| 5,288,078 | A | 2/1994 | Capper et al. |
| 5,524,637 | A | 6/1996 | Erickson |
| 5,616,078 | A | 4/1997 | Oh |
| 5,890,128 | A | 3/1999 | Diaz et al. |
| 6,308,565 | B1 | 10/2001 | French et al. |
| 6,430,997 | B1 | 8/2002 | French et al. |
| 6,571,111 | B1 | 5/2003 | Mayo et al. |
| 6,765,726 | B2 | 7/2004 | French et al. |
| 6,997,882 | B1 | 2/2006 | Parker et al. |
| 7,927,253 | B2 | 4/2011 | Vincent et al. |
| 8,075,450 | B2 | 12/2011 | Fabbri et al. |
| 8,083,647 | B2 | 12/2011 | Park |
| 8,548,770 | B2 | 10/2013 | Yuen et al. |
| 8,849,610 | B2 | 9/2014 | Molettiere et al. |
| 8,892,219 | B2 | 11/2014 | Pryor |
| 8,979,710 | B2 | 3/2015 | McCready et al. |
| 9,011,293 | B2 | 4/2015 | Shavit et al. |
| 9,076,226 | B2 | 7/2015 | Yang et al. |
| 9,323,868 | B2 | 4/2016 | Balakrishnan et al. |
| 9,369,365 | B2 | 6/2016 | Molettiere et al. |
| 9,852,271 | B2 | 12/2017 | Aragones et al. |
| 10,136,840 | B2 | 11/2018 | Guerrero et al. |
| 10,420,982 | B2 | 9/2019 | Aragones et al. |
| 11,045,114 | B2 | 6/2021 | Guerrero et al. |
| 2004/0063480 | A1 | 4/2004 | Wang |
| 2008/0022348 | A1 | 1/2008 | Shen |
| 2008/0319829 | A1 | 12/2008 | Hunt et al. |
| 2009/0048044 | A1 | 2/2009 | Oleson et al. |
| 2009/0138636 | A1 | 5/2009 | Burton et al. |
| 2009/0171614 | A1 | 7/2009 | Damen |
| 2009/0233769 | A1 | 9/2009 | Pryor |
| 2009/0262088 | A1 | 10/2009 | Moll-Carrillo et al. |
| 2010/0048357 | A1 | 2/2010 | Nakagawa et al. |
| 2010/0048358 | A1 | 2/2010 | Tchao et al. |
| 2010/0311544 | A1 | 12/2010 | Robinette et al. |
| 2011/0054870 | A1 | 3/2011 | Dariush et al. |
| 2011/0214030 | A1 | 9/2011 | Greenberg et al. |
| 2011/0306468 | A1 | 12/2011 | Wilson et al. |
| 2012/0143358 | A1 | 6/2012 | Adams et al. |
| 2012/0190505 | A1 | 7/2012 | Shavit et al. |
| 2012/0290594 | A1 | 11/2012 | Callahan |
| 2013/0070968 | A1 | 3/2013 | Yang et al. |
| 2013/0106684 | A1 | 5/2013 | Weast et al. |
| 2013/0190135 | A1 | 7/2013 | Pryor |
| 2013/0191034 | A1 | 7/2013 | Weast et al. |
| 2013/0196298 | A1 | 8/2013 | Watterson et al. |
| 2013/0197679 | A1 | 8/2013 | Balakrishnan et al. |
| 2013/0218585 | A1 | 8/2013 | Watterson |
| 2013/0237775 | A1 | 9/2013 | Gross |
| 2013/0249708 | A1 | 9/2013 | Moll-Carrillo et al. |
| 2013/0268205 | A1 | 10/2013 | Aragones et al. |
| 2013/0325396 | A1 | 12/2013 | Yuen et al. |
| 2013/0325399 | A1 | 12/2013 | Yuen et al. |
| 2014/0035761 | A1 | 2/2014 | Burton et al. |
| 2014/0039841 | A1 | 2/2014 | Yuen et al. |
| 2014/0142864 | A1 | 5/2014 | Spears et al. |
| 2014/0235171 | A1 | 8/2014 | Molettiere et al. |
| 2014/0270375 | A1 | 9/2014 | Canavan et al. |
| 2014/0274567 | A1 * | 9/2014 | McCready ......... A63B 71/0622 482/8 |
| 2014/0320310 | A1 | 10/2014 | Steinhardt |
| 2014/0349256 | A1 | 11/2014 | Connor |
| 2015/0044648 | A1 * | 2/2015 | White .................... G16H 40/63 434/236 |
| 2015/0046179 | A1 | 2/2015 | Kang |

FOREIGN PATENT DOCUMENTS

| | | | |
|---|---|---|---|
| JP | 2000070242 | A | 3/2000 |
| JP | 2001299732 | A | 10/2001 |
| JP | 2001309906 | A | 11/2001 |
| JP | 2001314375 | A | 11/2001 |
| JP | 2002112984 | A | 4/2002 |
| JP | 2005296649 | A | 10/2005 |
| JP | 2013138870 | A | 7/2013 |
| JP | 2015509019 | A | 3/2015 |
| WO | 2010096691 | A2 | 8/2010 |
| WO | 2012061804 | A1 | 5/2012 |
| WO | 2012071548 | A1 | 5/2012 |
| WO | 2012082782 | A1 | 6/2012 |
| WO | 2012093397 | A2 | 7/2012 |

OTHER PUBLICATIONS

"You can use your iFit membership on all types of iFit equipment—iFit", source : https//ifit.zendesk.com/hc/en-us/articles/201799690-You-can-use-your-iFit-membership-on-all-types-of-iFit-equipment Published Nov. 28, 2011.

"Equipment Support—iFit Live", source:http://222.ifit.com/iFitLive/supportifitLiveEquipmentSupport.do Accessed Feb. 3, 2010 via archive.org.

Sep. 26, 2017—(EP) ESR—App. No. 14796328.4.

* cited by examiner

136

FITNESS TRAINING SYSTEM FOR MERGING ENERGY EXPENDITURE CALCULATIONS FROM MULTIPLE DEVICES

CROSS-REFERENCE TO RELATED APPLICATIONS

The present application is a continuation of U.S. patent application Ser. No. 18/157,290, filed Jan. 20, 2023, which is a continuation of U.S. patent application Ser. No. 17/352,932, filed Jun. 21, 2021, now U.S. Pat. No. 11,564,597 issued Jan. 31, 2023, which is a continuation of U.S. patent application Ser. No. 16/199,874, filed Nov. 26, 2018, now U.S. Pat. No. 11,045,114 issued Jun. 29, 2021, which is a continuation of U.S. patent application Ser. No. 14/513,540, filed on Oct. 14, 2014, now U.S. Pat. No. 10,136,840 issued Nov. 27, 2018, which claims benefit to U.S. Provisional Application No. 61/890,672, filed Oct. 14, 2013, all of which are incorporated by reference herein in their entirety for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this clear separation between athletic activity and other activities reduces the amount of motivation that an individual might have toward exercising. Further, athletic activity services and systems directed toward encouraging individuals to engage in athletic activities might also be too focused on one or more particular activities while an individual's interest are ignored. This may further decrease a user's interest in participating in athletic activities or using the athletic activity services and systems.

Therefore, improved systems and methods to address these and other shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of this disclosure relate to processing of data taken while a user performs an athletic activity to determine an estimate of energy expenditure such as, for example, an amount of calories burned.

An illustrative apparatus for use with a user performing an exercise may include at least one processor, a first sensor, a communication circuit and at least one tangible memory. In some cases, the first sensor may be configured to monitor a first exercise performed by the user. The communication circuit may be configured to communicate at least energy expenditure information between the apparatus and at least a second device, the energy expenditure information including at least a first energy expenditure estimate corresponding to the first exercise monitored by the first sensor and a second energy expenditure estimate corresponding to a second exercise monitored by at least the second device. In some cases, the at least one tangible memory may be store computer-executable instructions that, when executed by the at least one processor, cause the apparatus at least to monitor, with the sensor, the first exercise performed by the user and/or determine, by the at least one processor, the first energy expenditure estimate of the user corresponding to the monitored first exercise. In some cases, the computer-executable instructions, when executed by the processor, may cause the illustrative apparatus to communicate, by the communication circuit, energy expenditure information between the apparatus and at least the second device. The energy expenditure information may include the first energy expenditure estimate and the second energy expenditure estimate. The computer-executable instructions, when executed by the processor, may further cause the illustrative apparatus to determine, by the at least one processor, a combined energy expenditure estimate of the user based, at least in part, on the first energy expenditure estimate and the second energy expenditure estimate.

In some cases, an illustrative system may include at least a first monitoring device configured to determine a first energy expenditure estimate associated with athletic activity performed by a user over a first duration and a second device, in communication with the first monitoring device, the second device configured to store at least a second energy expenditure estimate associated with athletic activity performed by the same user over a second duration. The first monitoring device may include a first processor and a first tangible memory device. In some cases, the first tangible memory device may store computer-executable instructions that, when executed by the first processor, may cause the first monitoring device at least to send, the first energy expenditure estimate to the second device, receive the second energy expenditure estimate from the second device, and determine, by the processor, a total energy expenditure estimate based, at least in part, on the first energy expenditure estimate and the second energy expenditure estimate. In some cases, the illustrative system may include a display to display the total energy expenditure estimate to the user.

Illustrative embodiments may relate to a system, method, apparatus, and computer readable media configured for determining first energy expenditure information associated with a first athletic activity of the user, synchronizing the first energy expenditure information with second energy expenditure information of a second device, determining a total energy expenditure estimate based, at least in part, on the first energy expenditure information and the second energy expenditure information, and displaying the total energy expenditure estimate, such as to a user. In some cases, the first energy expenditure information and/or the second energy expenditure information may include a first energy expenditure estimate and a first time stamp associated with the first athletic activity, These and other aspects of the embodiments are discussed in greater detail throughout this disclosure, including the accompanying drawings.

BRIEF DESCRIPTION OF THE DRAWINGS

The present disclosure is illustrated by way of example and not limited in the accompanying figures in which like reference numerals indicate similar elements and in which:

FIGS. 1A-B illustrate an example of a system for providing personal training in accordance with example embodiments, wherein FIG. 1A illustrates an example network configured to monitor athletic activity, and FIG. 1B illustrates an example computing device in accordance with example embodiments.

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

I. Example Personal Training System

A. Illustrative Computing Devices

Figure 1A:
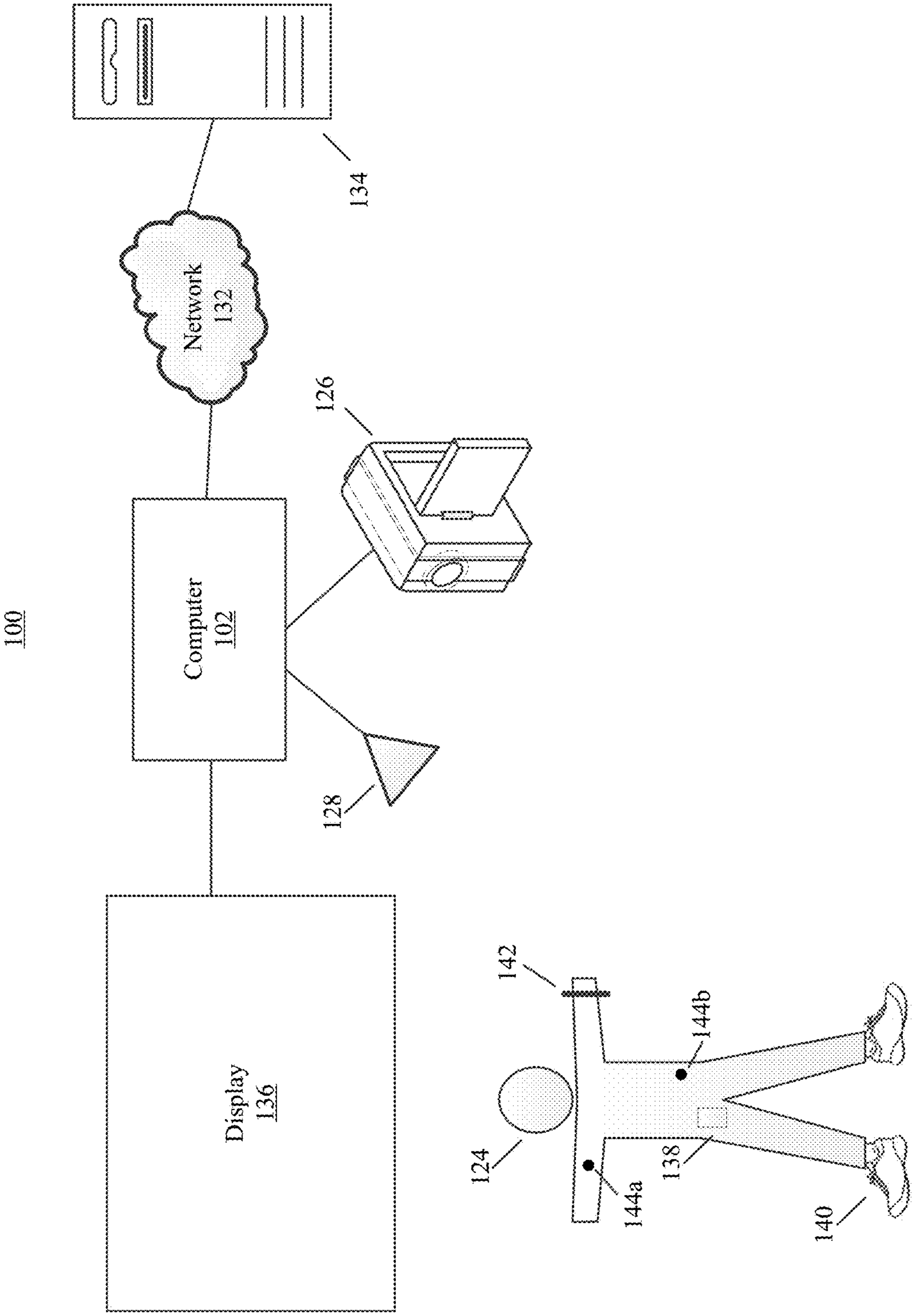

FIG. 1A illustrates an example of a personal training system 100 in accordance with example embodiments. Example system 100 may include one or more electronic devices, such as computer 102. Computer 102 may comprise a mobile terminal, such as a telephone, music player, tablet, netbook or any portable device. In other embodiments, computer 102 may comprise a set-top box (STB), desktop computer, digital video recorder(s) (DVR), computer server (s), and/or any other desired computing device. In certain configurations, computer 102 may comprise a gaming console, such as for example, a Microsoft® XBOX, Sony® Playstation, and/or a Nintendo® Wii gaming consoles. Those skilled in the art will appreciate that these are merely example consoles for descriptive purposes and this disclosure is not limited to any console or device.

Figure 1B:
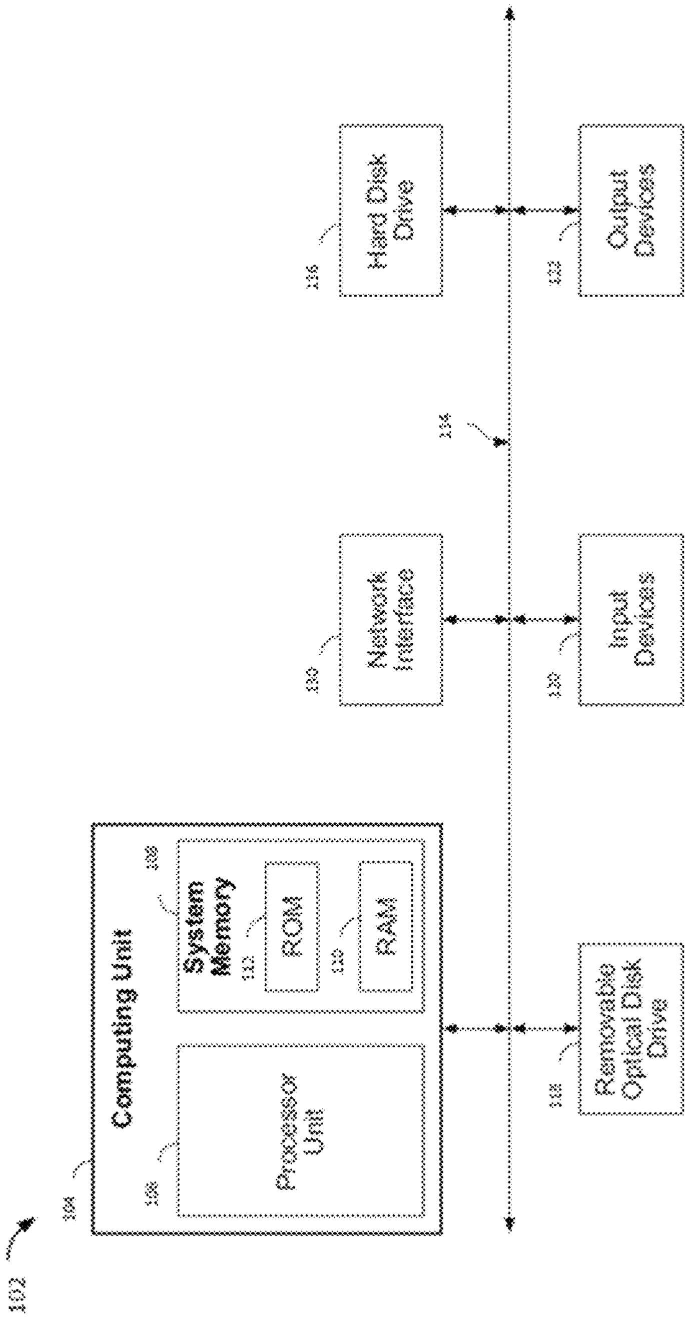

Turning briefly to FIG. 1B, computer 102 may include computing unit 104, which may comprise at least one processing unit 106. Processing unit 106 may be any type of processing device for executing software instructions, such as for example, a microprocessor device. Computer 102 may include a variety of non-transitory computer readable media, such as memory 108. Memory 108 may include, but is not limited to, random access memory (RAM) such as RAM 110, and/or read only memory (ROM), such as ROM 112. Memory 108 may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by computer 102.

The processing unit 106 and the system memory 108 may be connected, either directly or indirectly, through a bus 114 or alternate communication structure to one or more peripheral devices. For example, the processing unit 106 or the system memory 108 may be directly or indirectly connected to additional memory storage, such as a hard disk drive 116, a removable magnetic disk drive, an optical disk drive 118, and a flash memory card. The processing unit 106 and the system memory 108 also may be directly or indirectly connected to one or more input devices 120 and one or more output devices 122. The output devices 122 may include, for example, a display device 136, television, printer, stereo, or speakers. In some embodiments one or more display devices may be incorporated into eyewear. The display devices incorporated into eyewear may provide feedback to users. Eyewear incorporating one or more display devices also provides for a portable display system. The input devices 120 may include, for example, a keyboard, touch screen, a remote control pad, a pointing device (such as a mouse, touchpad, stylus, trackball, or joystick), a scanner, a camera or a microphone. In this regard, input devices 120 may comprise one or more sensors configured to sense, detect, and/or measure athletic movement from a user, such as user 124, shown in FIG. 1A.

Looking again to FIG. 1A, image-capturing device 126 and/or sensor 128 may be utilized in detecting and/or measuring athletic movements of user 124. In one embodiment, data obtained from image-capturing device 126 or sensor 128 may directly detect athletic movements, such that the data obtained from image-capturing device 126 or sensor 128 is directly correlated to a motion parameter. For example, and with reference to FIG. 4, image data from image-capturing device 126 may detect that the distance between sensor locations 402*g* and 402*i* has decreased and therefore, image-capturing device 126 alone may be configured to detect that user's 124 right arm has moved. Yet, in other embodiments, data from image-capturing device 126 and/or sensor 128 may be utilized in combination, either with each other or with other sensors to detect and/or measure movements. Thus, certain measurements may be determined from combining data obtained from two or more devices. Image-capturing device 126 and/or sensor 128 may include or be operatively connected to one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Example uses of illustrative sensors 126, 128 are provided below in Section I.C, entitled "Illustrative Sensors." Computer 102 may also use touch screens or image capturing device to determine where a user is pointing to make selections from a graphical user interface. One or more embodiments may utilize one or more wired and/or wireless technologies, alone or in combination, wherein examples of wireless technologies include Bluetooth® technologies, Bluetooth® low energy technologies, and/or ANT technologies.

B. Illustrative Network

Still further, computer 102, computing unit 104, and/or any other electronic devices may be directly or indirectly connected to one or more network interfaces, such as example interface 130 (shown in FIG. 1B) for communicating with a network, such as network 132. In the example of FIG. 1B, network interface 130, may comprise a network adapter or network interface card (NIC) configured to translate data and control signals from the computing unit 104 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection. Network 132, however, may be any one or more information distribution network(s), of any type(s) or topology(s), alone or in combination(s), such as internet(s), intranet(s), cloud(s), LAN(s). Network 132 may be any one or more of cable, fiber, satellite, telephone, cellular, wireless, etc. Networks are well known in the art, and thus will not be discussed here in more detail. Network 132 may be variously configured such as having one or more wired or wireless communication channels to connect one or more locations (e.g., schools, businesses, homes, consumer dwellings, network resources, etc.), to one or more remote servers 134, or to other computers, such as similar or identical to computer 102. Indeed, system 100 may include more than one instance of each component (e.g., more than one computer 102, more than one display 136, etc.).

Regardless of whether computer 102 or other electronic device within network 132 is portable or at a fixed location, it should be appreciated that, in addition to the input, output and storage peripheral devices specifically listed above, the computing device may be connected, such as either directly, or through network 132 to a variety of other peripheral devices, including some that may perform input, output and storage functions, or some combination thereof. In certain embodiments, a single device may integrate one or more components shown in FIG. 1A. For example, a single device may include computer 102, image-capturing device 126, sensor 128, display 136 and/or additional components. In one embodiment, sensor device 138 may comprise a mobile terminal having a display 136, image-capturing device 126, and one or more sensors 128. Yet, in another embodiment, image-capturing device 126, and/or sensor 128 may be peripherals configured to be operatively connected to a media device, including for example, a gaming or media system. Thus, it goes from the foregoing that this disclosure is not limited to stationary systems and methods. Rather, certain embodiments may be carried out by a user 124 in almost any location.

C. Illustrative Sensors

Computer 102 and/or other devices may comprise one or more sensors 126, 128 configured to detect and/or monitor at least one fitness parameter of a user 124. Sensors 126 and/or 128 may include, but are not limited to: an accelerometer, a gyroscope, a location-determining device (e.g., GPS), light sensor, temperature sensor (including ambient temperature and/or body temperature), sleep pattern sensors, heart rate monitor, image-capturing sensor, moisture sensor and/or combinations thereof. Network 132 and/or computer 102 may be in communication with one or more electronic devices of system 100, including for example, display 136, an image capturing device 126 (e.g., one or more video cameras), and sensor 128, which may be an infrared (IR) device. In one embodiment sensor 128 may comprise an IR transceiver. For example, sensors 126, and/or 128 may transmit waveforms into the environment, including towards the direction of user 124 and receive a "reflection" or otherwise detect alterations of those released waveforms. In yet another embodiment, image-capturing device 126 and/or sensor 128 may be configured to transmit and/or receive other wireless signals, such as radar, sonar, and/or audible information. Those skilled in the art will readily appreciate that signals corresponding to a multitude of different data spectrums may be utilized in accordance with various embodiments. In this regard, sensors 126 and/or 128 may detect waveforms emitted from external sources (e.g., not system 100). For example, sensors 126 and/or 128 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology. As a non-limited example, image-capturing devices configured to perform range phenomenology are commercially available from Flir Systems, Inc. of Portland, Oregon. Although image capturing device 126 and sensor 128 and display 136 are shown in direct (wirelessly or wired) communication with computer 102, those skilled in the art will appreciate that any may directly communicate (wirelessly or wired) with network 132.

1. Multi-Purpose Electronic Devices

User 124 may possess, carry, and/or wear any number of electronic devices, including sensory devices 138, 140, 142, and/or 144. In certain embodiments, one or more devices 138, 140, 142, 144 may not be specially manufactured for fitness or athletic purposes. Indeed, aspects of this disclosure relate to utilizing data from a plurality of devices, some of which are not fitness devices, to collect, detect, and/or measure athletic data. In one embodiment, device 138 may comprise a portable electronic device, such as a telephone or digital music player, including an IPOD®, IPAD®, or iPhone®, brand devices available from Apple, Inc. of Cupertino, California, devices operating using the Android® platform available from Google, Inc. of Mountain View, California, or Zune® or Microsoft® Windows devices available from Microsoft of Redmond, Washington, or the like. As known in the art, digital media players can serve as both an output device for a computer (e.g., outputting music from a sound file or pictures from an image file) and a storage device. In one embodiment, device 138 may be computer 102, yet in other embodiments, computer 102 may be entirely distinct from device 138. Regardless of whether device 138 is configured to provide certain output, it may serve as an input device for receiving sensory information. Devices 138, 140, 142, and/or 144 may include one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In certain embodiments, sensors may be passive, such as reflective materials that may be detected by image-capturing device 126 and/or sensor 128 (among others). In certain embodiments, sensors 144 may be integrated into apparel, such as athletic clothing. For instance, the user 124 may wear one or more on-body sensors 144*a-b*. Sensors 144 may be incorporated into the clothing of user 124 and/or placed at any desired location of the body of user 124. Sensors 144 may communicate (e.g., wirelessly) with computer 102, sensors 128, 138, 140, and 142, and/or camera 126. Examples of interactive gaming apparel are described in U.S. patent application Ser. No. 10/286,396, filed Oct. 30, 2002, and published as U.S. Pat. Pub, No. 2004/0087366, the contents of which are incorporated herein by reference in its entirety for any and all non-limiting purposes. In certain embodiments, passive sensing surfaces may reflect waveforms, such as infrared light, emitted by image-capturing device 126 and/or sensor 128. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration.

Devices 138-144 may communicate with each other, either directly or through a network, such as network 132. Communication between one or more of devices 138-144 may communicate through computer 102. For example, two or more of devices 138-144 may be peripherals operatively connected to bus 114 of computer 102. In yet another embodiment, a first device, such as device 138 may communicate with a first computer, such as computer 102 as well as another device, such as device 142, however, device 142 may not be configured to connect to computer 102 but may communicate with device 138. Those skilled in the art will appreciate that other configurations are possible.

Some implementations of the example embodiments may alternately or additionally employ computing devices that are intended to be capable of a wide variety of functions, such as a desktop or laptop personal computer. These computing devices may have any combination of peripheral devices or additional components as desired. Also, the components shown in FIG. 1B may be included in the server 134, other computers, apparatuses, etc.

2. Illustrative Apparel/Accessory Sensors

In certain embodiments, sensory devices 138, 140, 142 and/or 144 may be formed within or otherwise associated with user's 124 clothing or accessories, including a watch, armband, wristband, necklace, shirt, shoe, or the like. Examples of shoe-mounted and wrist-worn devices (devices 140 and 142, respectively) are described immediately below, however, these are merely example embodiments and this disclosure should not be limited to such.

i. Shoe-Mounted Device

In certain embodiments, sensory device 140 may comprise footwear which may include one or more sensors, including but not limited to: an accelerometer, location-sensing components, such as GPS, and/or a force sensor system. FIG. 2A illustrates one example embodiment of a sensor system 202. In certain embodiments, system 202 may include a sensor assembly 204. Assembly 204 may comprise one or more sensors, such as for example, an accelerometer, location-determining components, and/or force sensors. In the illustrated embodiment, assembly 204 incorporates a plurality of sensors, which may include force-sensitive resistor (FSR) sensors 206. In yet other embodiments, other sensor(s) may be utilized. Port 208 may be positioned within a sole structure 209 of a shoe. Port 208 may optionally be provided to be in communication with an electronic module 210 (which may be in a housing 211) and a plurality of leads 212 connecting the FSR sensors 206 to the port 208. Module 210 may be contained within a well or cavity in a sole structure of a shoe. The port 208 and the module 210 include complementary interfaces 214, 216 for connection and communication.

In certain embodiments, at least one force-sensitive resistor 206 shown in FIG. 2A may contain first and second electrodes or electrical contacts 218, 220 and a force-sensitive resistive material 222 disposed between the electrodes 218, 220 to electrically connect the electrodes 218, 220 together. When pressure is applied to the force-sensitive material 222, the resistivity and/or conductivity of the force-sensitive material 222 changes, which changes the electrical potential between the electrodes 218, 220. The change in resistance can be detected by the sensor system 202 to detect the force applied on the sensor 216. The force-sensitive resistive material 222 may change its resistance under pressure in a variety of ways. For example, the force-sensitive material 222 may have an internal resistance that decreases when the material is compressed, similar to the quantum tunneling composites described in greater detail below. Further compression of this material may further decrease the resistance, allowing quantitative measurements, as well as binary (on/off) measurements. In some circumstances, this type of force-sensitive resistive behavior may be described as "volume-based resistance," and materials exhibiting this behavior may be referred to as "smart materials." As another example, the material 222 may change the resistance by changing the degree of surface-to-surface contact. This can be achieved in several ways, such as by using microprojections on the surface that raise the surface resistance in an uncompressed condition, where the surface resistance decreases when the microprojections are compressed, or by using a flexible electrode that can be deformed to create increased surface-to-surface contact with another electrode. This surface resistance may be the resistance between the material 222 and the electrode 218, 220 222 and/or the surface resistance between a conducting layer (e.g., carbon/graphite) and a force-sensitive layer (e.g., a semiconductor) of a multi-layer material 222. The greater the compression, the greater the surface-to-surface contact, resulting in lower resistance and enabling quantitative measurement. In some circumstances, this type of force-sensitive resistive behavior may be described as "contact-based resistance." It is understood that the force-sensitive resistive material 222, as defined herein, may be or include a doped or non-doped semiconducting material.

The electrodes 218, 220 of the FSR sensor 216 can be formed of any conductive material, including metals, carbon/graphite fibers or composites, other conductive composites, conductive polymers or polymers containing a conductive material, conductive ceramics, doped semiconductors, or any other conductive material. The leads 212 can be connected to the electrodes 218, 220 by any suitable method, including welding, soldering, brazing, adhesively joining, fasteners, or any other integral or non-integral joining method. Alternately, the electrode 218, 220 and associated lead 212 may be formed of a single piece of the same material.

ii. Wrist-Worn Device

Figure 2B:
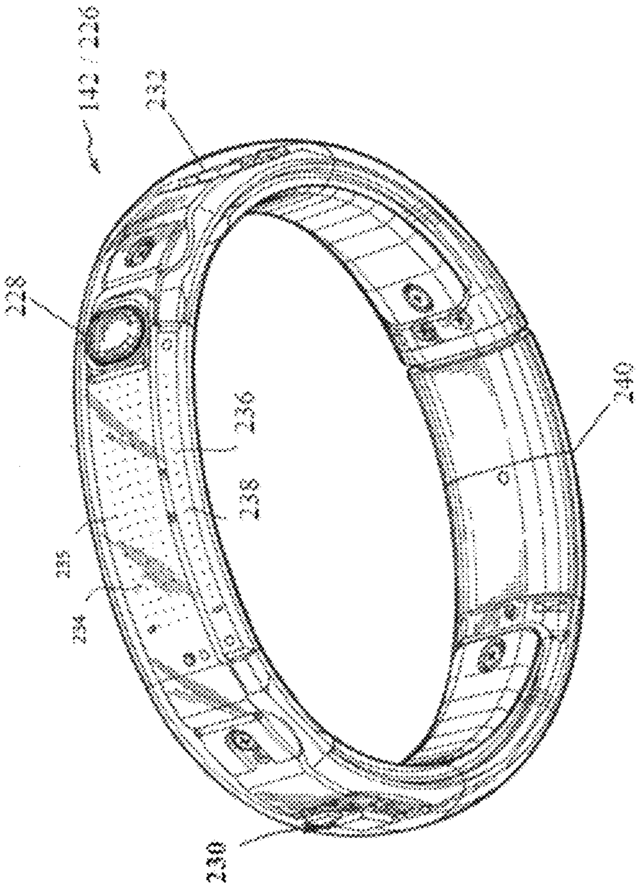
FIGS. 2A-B illustrate example sensor assemblies that may be worn by a user in accordance with example embodiments.
Figure 2A:
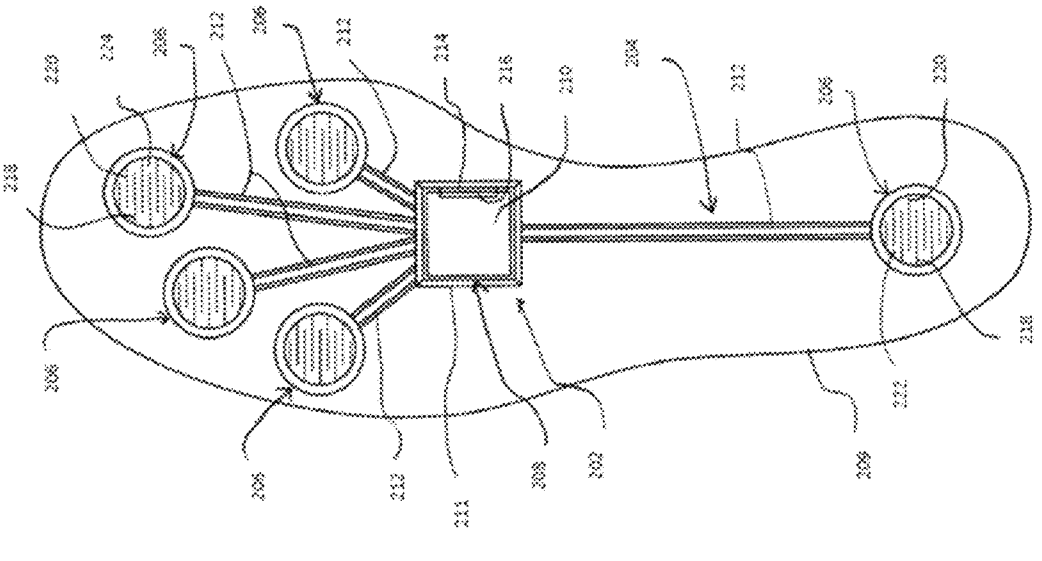

As shown in FIG. 2B, device 226 (which may resemble or be sensory device 142 shown in FIG. 1A) may be configured to be worn by user 124, such as around a wrist, arm, ankle or the like. Device 226 may monitor athletic movements of a user, including all-day activity of user 124. In this regard, device assembly 226 may detect athletic movement during user's 124 interactions with computer 102 and/or operate independently of computer 102. For example, in one embodiment, device 226 may be an-all day activity monitor that measures activity regardless of the user's proximity or interactions with computer 102. Device 226 may communicate directly with network 132 and/or other devices, such as devices 138 and/or 140. In other embodiments, athletic data obtained from device 226 may be utilized in determinations conducted by computer 102, such as determinations relating to which exercise programs are presented to user 124. In one embodiment, device 226 may also wirelessly interact with a mobile device, such as device 138 associated with user 124 or a remote website such as a site dedicated to fitness or health related subject matter. At some predetermined time, the user may wish to transfer data from the device 226 to another location.

As shown in FIG. 2B, device 226 may include an input mechanism, such as a depressible input button 228 assist in operation of the device 226. The input button 228 may be operably connected to a controller 230 and/or any other electronic components, such as one or more of the elements discussed in relation to computer 102 shown in FIG. 1B. Controller 230 may be embedded or otherwise part of housing 232. Housing 232 may be formed of one or more materials, including elastomeric components and comprise one or more displays, such as display 234. The display may be considered an illuminable portion of the device 226. The display 234 may include a series of individual lighting elements or light members such as LED lights 234 in an exemplary embodiment. The LED lights may be formed in an array and operably connected to the controller 230. Device 226 may include an indicator system 236, which may also be considered a portion or component of the overall display 234. It is understood that the indicator system 236 can operate and illuminate in conjunction with the display 234 (which may have pixel member 235) or completely separate from the display 234. The indicator system 236 may also include a plurality of additional lighting elements or light members 238, which may also take the form of LED lights in an exemplary embodiment. In certain embodiments, indicator system may provide a visual indication of goals, such as by illuminating a portion of lighting members 238 to represent accomplishment towards one or more goals.

A fastening mechanism 240 can be unlatched wherein the device 226 can be positioned around a wrist of the user 124 and the fastening mechanism 240 can be subsequently placed in a latched position. The user can wear the device 226 at all times if desired. In one embodiment, fastening mechanism 240 may comprise an interface, including but not limited to a USB port, for operative interaction with computer 102 and/or devices 138, 140.

In certain embodiments, device 226 may comprise a sensor assembly (not shown in FIG. 2B). The sensor assembly may comprise a plurality of different sensors. In an example embodiment, the sensor assembly may comprise or permit operative connection to an accelerometer (including in the form of a multi-axis accelerometer), heart rate sensor, location-determining sensor, such as a GPS sensor, and/or other sensors. Detected movements or parameters from device's 142 sensor(s), may include (or be used to form) a variety of different parameters, metrics or physiological characteristics including but not limited to speed, distance, steps taken, and energy expenditure such as calories, heart rate, sweat detection, effort, oxygen consumed, and/or oxygen kinetics. Such parameters may also be expressed in terms of activity points or currency earned by the user based on the activity of the user.

I. Illustrative Athletic Monitoring Methods

System 100 may prompt a user to perform one or more exercises, monitor user movement while performing the exercises, and provide the user with an energy expenditure estimate based on their movement. System 100 may analyze a user's form to determine if the user is making an exercise more or less difficult, and adjust the energy expenditure estimate accordingly. Energy expenditure estimates may be, or comprise, an estimate of calories burned by the user. In certain embodiments, energy expenditure determinations may be based on, and/or conveyed as a point system. In one embodiment, calories may be converted to a point system, yet in other embodiments, measurements may be directly obtained in one or more point systems. In one implementation, activity points may be based upon: form, body movements, and/or completion of certain activities. In further embodiments, energy expenditure calculations may comprise determinations relating to: effort, oxygen consumed, and/or oxygen kinetics of the user. In one embodiment, computer 102, camera 126, sensor 128, and display 136 may be implemented within the confines of a user's residence, although other locations, including gyms and/or businesses are contemplated. Further, as discussed above, computer 102 may be a portable device, such as a cellular telephone, therefore, one or more aspects discussed herein may be conducted in almost any location. In this regard, the example embodiments of this disclosure are discussed in the context of being implemented with one or more of the example components of system 100. Those skilled in the art will appreciate that reference(s) to a particular component, such as computer 102, is not meant to be limiting, but rather to provide an illustrative example of one of many possible implementations. Thus, although certain components may be referenced, it is to be assumed that other components of system 100 may be utilized unless expressly disclaimed or physically impossible. Further, aspects disclosed herein are not limited to example system 100.

A. Monitoring User Movements

Figure 3:
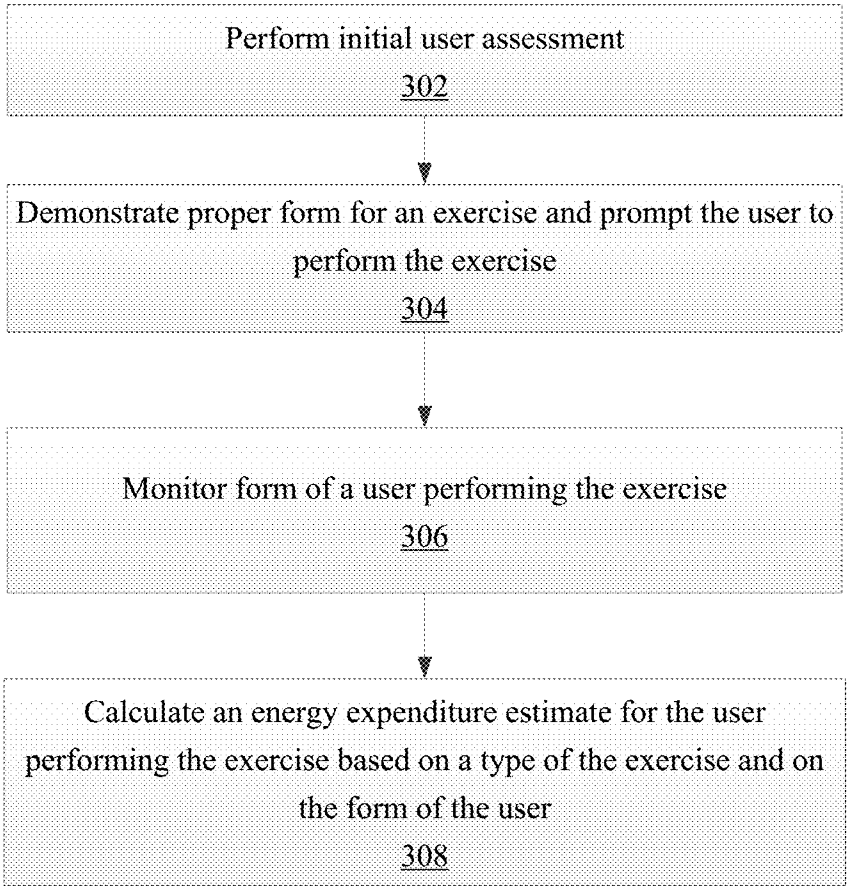
FIG. 3 illustrates an example flow diagram of a method for calculating an energy expenditure estimate for a user that accounts for a user's form while exercising as part of the estimate, in accordance with example embodiments.

While exercising, the system 100 may use one or more techniques to monitor user movement. FIG. 3 illustrates an example flow diagram of a method for calculating an energy expenditure estimate for a user that accounts for a user's form while exercising as part of the estimate, in accordance with example embodiments. The method may be implemented by a computer, such as, for example, computer 102, device 138, 140 and/or 142, as well as or other apparatuses. The blocks shown in FIG. 3 may be rearranged, some blocks may be removed, additional blocks may be added, each block may be repeated one or more times, and the flow diagram may be repeated one or more times. The flow diagram may begin at block 302.

1. Perform User Assessment

In block 302, the method may include performing an initial assessment of the user. A user, such as user 124, may be positioned in range of a sensor, such as in front of the image capturing device 126 and/or sensor 128, which may comprise an infrared transceiver. Display 136 may present a representation of user 124 that may be a "mirror-image" or depict a virtual avatar, such as a user avatar, that moves to correspond with user movement. Computer 102 may prompt the user to move into a certain region relative to the image capturing device 126 and/or relative to the infrared transceiver 128 so that the user is within frame and/or range. When properly positioned, system 100 may process movement of the user. Although the term "initial" has been utilized, this assessment may occur each time the user initiates system 100, performs certain movements, upon passage of time, or for any other reason. Thus, references to assessments herein are not limited to a single assessment.

a. Identify Sensory Locations

Figure 4:
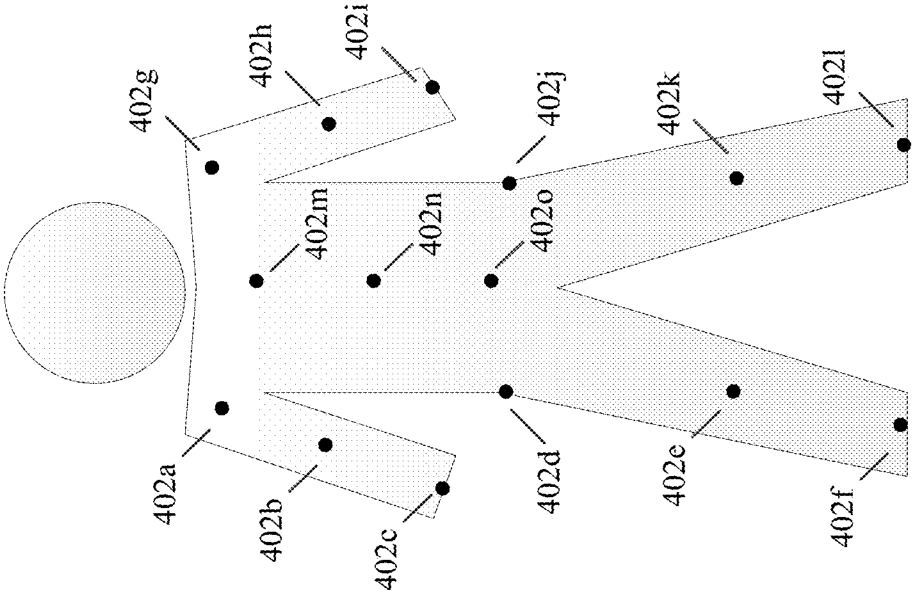
FIG. 4 illustrates example points on a user's body for monitoring during exercising in accordance with example embodiments.

System 100 may process sensory data to identify user movement data. In one embodiment, sensory locations on a user's body may be identified. With reference to FIG. 4, sensory locations 402*a*-4020 may correspond to locations of interest on the user's 124 body (e.g., ankles, elbows, shoulders, etc.). For example, images of recorded video, such as from camera 126, may be utilized in an identification of the sensory locations 402*a*-4020. For example, the user may stand a certain distance, which may or may not be predefined, from the camera 126, and system 100 may process the images to identify the user 124 within the video, for example, using disparity mapping techniques. In an example, image capturing device 126 may be a stereo camera having two or more lenses that are spatially offset from one another and that simultaneously capture two or more images of the user. System 100 may process the two or more images taken at a same time instant to generate a disparity map for determining a location of certain parts of the user's body in each image (or at least some of the images) in the video using a coordinate system (e.g., Cartesian coordinates). The disparity map may indicate a difference between an image taken by each of the offset lenses.

In a second example, one or more sensors may be located on or proximate to the user's 124 body at the sensory locations 402*a*-4020 or the user 124 may wear a suit having sensors situated at various locations. Yet, in other embodiments, sensor locations may be determined from other sensory devices, such as devices 138, 140 and/or 142. In this regard, sensors may be physical sensors located on a user's clothing, yet in other embodiments, sensor locations 402*a*-4020 may be based upon identification of relationships between two moving body parts. For example, sensor location 402*a* may be determined by identifying motions of user 124. In this regard, the overall shape or portion of a user's body may permit identification of certain body parts. Regardless of whether a camera, such as camera 126, is utilized and/or a physical sensor located on the user 124, such as sensors within device(s) 138, 140, 142 are utilized, the sensors may sense a current location of a body part and/or track movement of the body part.

In certain embodiments, a time stamp may be added to the data collected (such as collected part of block 302 in FIG. 3) indicating a specific time when a body part was at a certain location. Sensor data may be received at computer 102 (or other device) via wireless or wired transmission. A computer, such as computer 102 and/or devices 138, 140, 142, may process the time stamps to determine the locations of the body parts using a coordinate system (e.g., Cartesian coordinates) within each (or at least some) of the images in the video. Data received from camera 126 may be corrected, modified, and/or combined with data received from one or more other devices 138, 140, and 142.

In a third example, system 100 may use infrared pattern recognition to detect user movement and locations of body parts of the user 124. For example, sensor 128 may include an infrared transceiver, which may be part of camera 126, or another device, that may emit an infrared signal to illuminate the user's 124 body using infrared signals. The infrared transceiver 128 may capture a reflection of the infrared signal from the body of user 124. Based on the reflection, the system 100 may identify a location of certain parts of the user's body using a coordinate system (e.g., Cartesian coordinates) at particular instances in time. Which and how body parts are identified may be predetermined based on a type or types of exercise a user is requested to perform.

Figure 5:
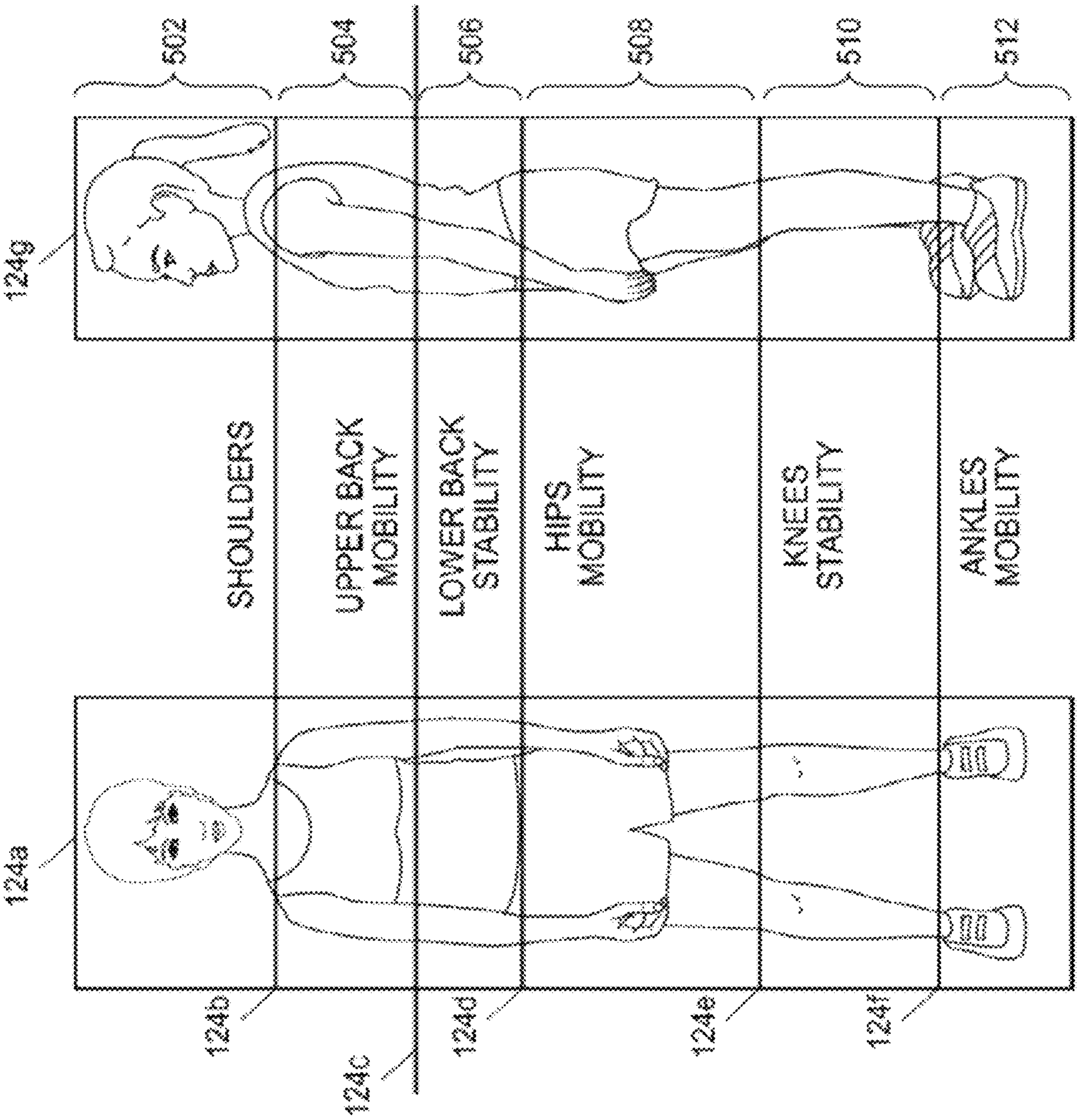
FIG. 5 illustrates an example posture assessment in accordance with example embodiments.

As part of a workout routine, system 100 may make an initial postural assessment of the user 124 as part of the initial user assessment in block 302 of FIG. 3. With reference to FIG. 5, system 100 may analyze front and side images of a user 124 to determine a location of one or more of a user's shoulders, upper back, lower back, hips, knees, and ankles. On-body sensors and/or infrared techniques may also be used, either alone or in conjunction with camera 126, to determine the locations of various body parts for the postural assessment. For example, system 100 may determine assessment lines 124*a*-*g* and/or regions 502-512 to determine the locations of a various points on a user's body, such as, for example, ankles, knees, hips, upper back, lower back, and shoulders.

b. Identify Sensory Regions

In further embodiments, system 100 may identify sensory regions (see, e.g., block 302). In one embodiment, assessments lines 124*a*-*g* may be utilized to divide the user's body into regions. For example, lines 124*b*-*f* may be horizontal axes. For example, a "shoulders" region 502 may correlate to a body portion having a lower boundary around the user's shoulders (see line 124*b*), region 504 may correlate to the body portion between the shoulders (line 124*b*) and about half the distance to the hips (see line 124*c*) and thus be an "upper back" region, and region 506 may span the area between line 124*c* to the hips (see line 124*d*) to comprise a "lower back region." Similarly, region 508 may span the area between the "hips" (line 124*d*) and the "knees" (see line 124*e*), region 510 may span between lines 124*e* and 124*f* and region 512 (see "ankles") may have an upper boundary around line 124*f*. Regions 502-512 may be further divided, such as into quadrants, such as by using axes 124*a* and 124*g*. To aid in the identification of one or more sensory regions, system 100 may prompt the user to make one or more specific movements. For example, system 100 may prompt a user to move a specific body part or region (e.g., waive their right arm, or waive the left arm in a specific pattern) to aid the system 100 (e.g., computer algorithm processing information received from the infrared transceiver 128) in determining which body part or region is in a specific location within a coordinate system.

c. Categorize Locations or Regions

In certain embodiments, body parts or regions that are not proximate to each other may nonetheless be categorized into the same movement category (see, e.g., block 302). For example, as shown in FIG. 5, the "upper back", "hips", and "ankles" regions 504, 508, 512 may be categorized as belonging to a "mobility" category. In another embodiment, the "lower back" and "knees" regions 506, 510 may be categorized as belonging to a "stability" category. The categorizations are merely examples, and in other embodiments, a location or region may belong to multiple categories. For example, a "center of gravity" region may be formed from regions 504 and 506. In one embodiment, a "center of gravity" may comprise portions of regions 504 and 506. In another embodiment, a "center of moment" category may be provided, either independently, or alternatively, as comprising a portion of at least another category. In one embodiment, a single location may be weighted in two or more categories, such as being 10% weighted in a "stability" category and 90% weighted in a "mobility" category.

System 100 may also process the image to determine a color of clothing of the user or other distinguishing features to differentiate the user from their surroundings. After processing, system 100 may identify a location of multiple points on the user's body and track locations of those points, such as locations 402 in FIG. 4. System 100 may also prompt the user to answer questions to supplement the postural assessment, such as, for example, age, weight, etc. Again, block 302 is optional and is not required in accordance with various embodiments.

2. Providing Form

With reference again to FIG. 3, in block 304, various embodiments may include demonstrating proper form for an exercise and prompting the user to perform the exercise. For example, after or in addition to the initial postural assessment, the system 100 (such as with computer 102) may cause the display 136 to present a virtual trainer demonstrating an exercise to instruct the user on proper form and/or may present a depiction and/or an actual video of a real person demonstrating proper form for an exercise. System 100 may then prompt the user to begin performing the exercise.

Figure 6:
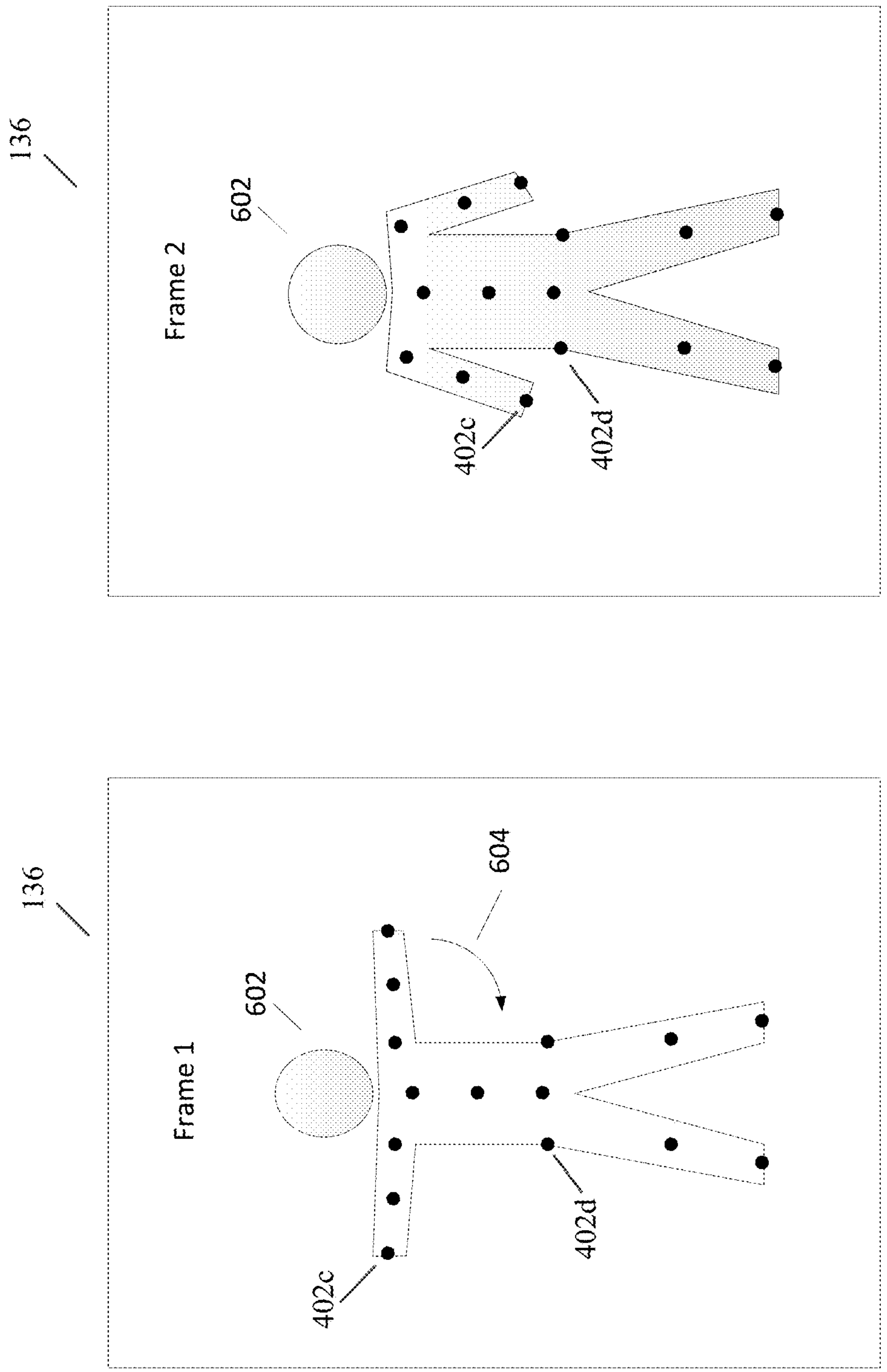
FIG. 6 illustrates example displays of a virtual avatar of a user performing an exercise in accordance with example embodiments.

With reference to FIG. 3, in block 306, various embodiments may include monitoring form of a user performing the exercise. As seen in FIG. 6, system 100, such as through computer 102, may cause the display 136 to present a virtual avatar 602 of the user. The virtual avatar 602 may move in synchronism with the user 124. Also, the display 136 may present video of the actual user, rather than avatar 602. System 100 may process one or more frames in the video to determine at least some of the sensory locations 402, or may receive data from sensors worn on-body by the user. As shown in FIG. 6, sensory locations 402 may be displayed on the virtual avatar.

For proper form during many exercise routines, a user may proceed through multiple positions during a repetition of an exercise. Certain aspects disclosed herein relate to defining one or more measurement positions and/or desired locations for one or more sensory locations 402. For example, a measurement position may refer to a particular relationship between various body parts during a repetition. For example, a measurement position may indicate a desired location for a user's body part (e.g., desired location of user's left elbow) and may indicate a desired relationship between multiple body parts (e.g., angle between a user's torso and thigh). For a movement or series of movements (such as an exercise routine), system 100 may define one or more measurement positions and/or desired locations for one or more of the sensory locations 402 for a measurement position. In various implementations, each repetition of an exercise can be broken down into one or more measurement positions.

System 100, such as through computer 102, may process video or sensor data of a user performing an exercise to determine when a user's body has reached a measurement position. For each measurement position, system 100 may compare the measured sensory locations to desired sensory locations to monitor the user's form while performing the exercise. For example, frame 1 of FIG. 6 may correspond to a first measurement position and frame 2 may correspond to a second measurement position. System 100 may determine a distance between sensory locations 402*c* and 402*d* at each measurement position. Other relationships between sensory locations may be specified (e.g., certain angle, certain position, etc.)

With reference again to FIG. 3, in block 308, various embodiments may include calculating an energy expenditure estimate for the user. Calculations may be based on a type of the exercise and/or on the form of the user. The energy expenditure estimate may be, or comprise, for example, an estimate of calories burned by the user. In certain embodiments, energy expenditure calculations comprise determinations relating to: effort, oxygen consumed, and/or oxygen kinetics of the user. During a workout session or upon its completion, the system 100 may inform the user of energy expended. In one embodiment, system 100 may provide an indication of a quantity of calories they have burned. To provide a more accurate calories burned estimate, system 100 may account for a user's form while performing an exercise as well as the type of exercise that was performed. Further embodiments may utilize user attributes to more accurately identify a number of calories burned by a user. Example user attributes may be height, weight, age, etc. One or more sensors may determine the user attributes, or the user may input the user attributes via an interface to a computer, such as computer 102.

System 100 may use information from sensory locations 402 detected at measurement positions of an exercise in combination with one or more known values to obtain a more accurate determination of calories burned. In one embodiment, a known value may comprise or be part of a Metabolic Equivalent of Task (MET) table. A MET table, for example, may be defined for a particular exercise (e.g., squat, lunge, etc.) and used to determine how many calories a user burned during a workout. System 100 may store or have access to multiple MET tables corresponding to different exercises (e.g., squat, lunge, jumping rope, push up, running, etc.). System 100 may process data from the video and/or sensors to determine a number of repetitions of an exercise that a user has performed or duration of an exercise, and may estimate a number of calories burned by the user based on the repetitions and/or duration information and the one or more known values, such as may be obtained from MET tables.

MET tables, however, are statistical averages and are not as accurate as they could be. Thus, conventional calorie measurement systems that rely on MET tables merely provide a user with a rough estimate of how many calories they burned during a workout. Although embodiments of this disclosure may utilize one or more values from a MET table, aspects of this disclosure are not limited by the deficiencies of prior measurements systems. For example, in one embodiment the user's form may be accounted for. System 100 may apply a scaling factor to a calories burned estimate based on detected sensory location information. The scaling factor may reflect how well a user has performed an exercise and in certain embodiments may consider attributes of the user. For example, the scaling factor may be a function of one or more of the sensory location information, a duration during which the user performed an exercise, information reported by the user (e.g., age, weight), a user's heart rate taken by a heart rate monitor, a pressure measurement, and/or other data. A pressure measurement may be obtained from pressure sensor 140 located in a shoe, for example, to determine how much force a user exerts during movement. For example, a user may be holding a weight in each hand and the pressure sensor 140 may monitor pressure at the shoe. The pressure sensor 140 may also indicate how quickly a user changes direction (e.g., how hard a user made a cut) or how much power was exerted when jumping.

To determine the scaling factor, system 100 may monitor for relationships between one or more body parts at one or more measurement positions during a repetition of an exercise. Modifications to these relationships may make an exercise easier or harder to perform. The scaling factor may consider factors indicative of whether a user is making the exercise more or less difficult to complete, and may adjust a calories burned estimate accordingly. In a squat, for example, relationships may be defined for a first angle between a user's torso and thighs, and a second angle between a user's thighs and shin while performing the squat. System 100 may process sensory location information to measure the first and second angle of the user over time for comparison with the desired first and second angle.

Figure 7A:
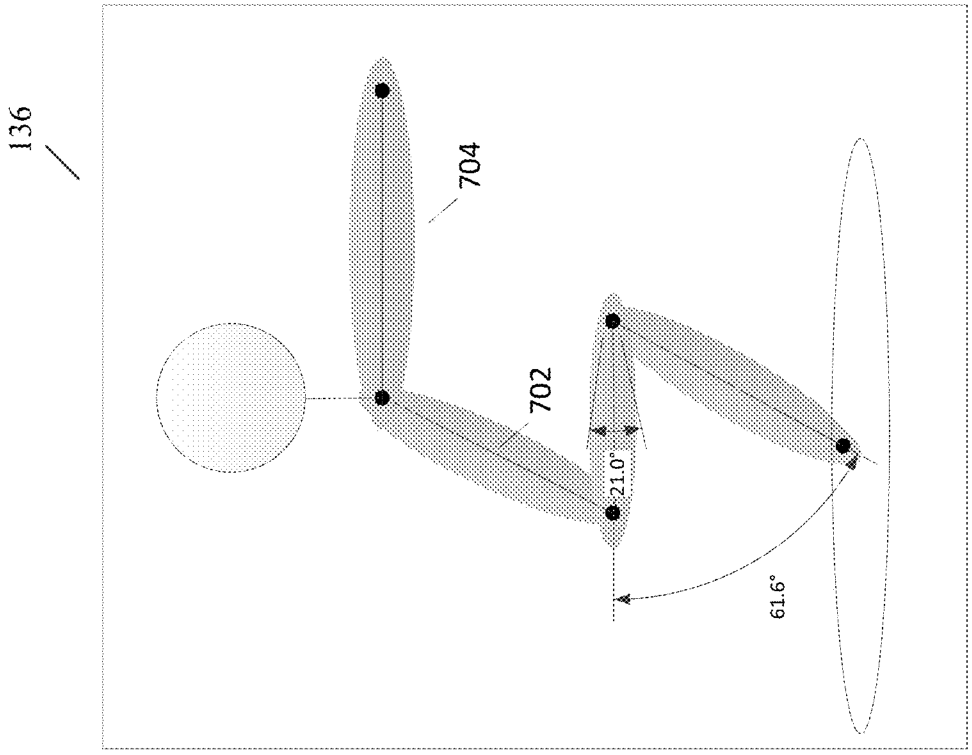
FIGS. 7A-B illustrate example displays of a virtual avatar of a user performing a squat in accordance with example embodiments.
Figure 7B:
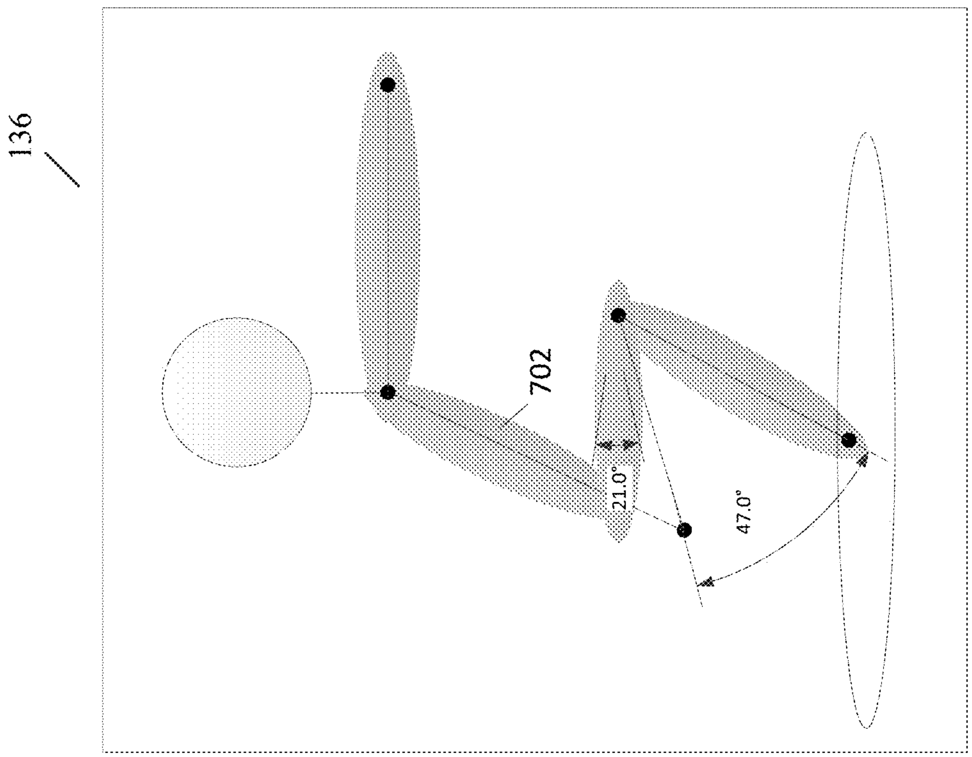

In an example, with reference to FIGS. 7A-B, a virtual avatar 702 of a user is displayed performing a squat. Virtual avatar 702 is depicted as a stick figure, and proper technique for an exercise is shown as a shaded region 704. At the lowest part of the squat (for example, as shown in FIG. 7A), the desired form may specify a relationship between a user's thigh and shin, between a user's back and arms, and/or any other two parts or locations the user. In one embodiment, the desired form may specify a first predetermined angle between a location or part. For example, a user's upper leg and lower leg, and/or a second predetermined angle between a user's back and arms. System 100 may process the sensory location information to compare the user's form to the desired form. For example, system 100 may process the sensory location information to determine an angle between the user's thigh and shin, and an angle between the user's back and arms when performing a squat.

System 100 may define thresholds for the relationships between various body parts for adjusting the scaling factor. The thresholds may permit the user's form to differ by a certain amount from the desired form. For a preferred threshold, system 100 may determine that the user has good form that does not require any adjustment of the scaling factor (e.g., less than a 5% difference between angle between the user's upper leg and lower leg and desired angle). For an acceptable threshold, the system 100 may nominally adjust the scaling factor upward or downward to reflect increased or reduced effort by the user (e.g., 5-15% difference between angle between the user's upper leg and lower leg and desired angle). For an unacceptable threshold, the system 100 may determine that the user's form has reduced the amount of effort to perform the exercise and may downwardly adjust the scaling factor (e.g., greater than a 15% difference between angle between the user's upper leg and lower leg and desired angle).

System 100 may also adjust the scaling factor based on omissions or additions a user makes when performing an exercise. For example, a user may not be doing an arm movement in an exercise that requires movement of both arms and legs. Also, if the user is performing an additional movement beyond what is specified for an exercise, the system 100 may adjust the scaling factor to increase the calorie estimate.

Upon determining the scaling factor, the system 100 may determine an amount of calories burned as a function of the scaling factor(s) and the calorie estimate. The function may be a multiplication of the calorie estimate by the scaling factor, or via other relationships. For example, the scaling factor may be adjustments to a number of variables in a mathematical equation for adjusting calories burned by one or more of multiplication, addition, and subtraction. In further embodiments, system 100 may cease determinations relating to caloric expenditure if the user deviates from a threshold. For example, a user may be interrupted during a workout routine and either forget or be too distracted to "pause" the determination, thus, certain embodiments may cease determining caloric expenditure upon detecting that a user is not performing an exercise. Further embodiments may cease or otherwise alter determinations of caloric expenditure if one or more variation thresholds are exceeded, such as for example, if a user is over-extending or under-extending a body region or part. In certain embodiments, if a user's movements are prone to cause injury, measurements and/or determinations relating to caloric expenditure may be stopped. In one implementation, system 100 may provide cues and/or instructions to correct the user's deficiencies or incorrect movements.

The following provides an example equation for calculating an amount of calories burned by a user during a workout.

$$\text{Calories burned} = BMR*(\text{Activity modifier})*(\text{Completeness modifier}). \quad \text{Equation (1)}$$

In equation (1), BMR is an acronym for Basal Metabolic Rate. The system 100 may calculate the BMR using the Mifflin-St. Jeor Equation, BMR=(10*w)+(6.25*h)−(5.0*a)+(5 for men, −161 for women), where "*" is the multiplication symbol, "w"=weight in kilograms, "h"=height in centimeters, "a"=age in years. The system 100 may also use the Harris-Benedict equation instead of or, in addition to, the Mifflin-St. Jeor Equation.

The activity modifier may be an adjustment corresponding to a type of exercise being performed by a user. The activity modifier may be larger for more strenuous exercises, and smaller for less strenuous. System 100 may store a file containing activity modifiers, where each activity modifier may have a value for a particular exercise type. Two or more exercises may have activity modifiers with a same value, or certain exercise may have a unique value for the activity modifier. The activity modifier may have a default value. In one example embodiment, the default value may be 0.1. In a second embodiment, the default value may be 1.0. The default value may be any value, including 0.0. System 100 may update the default value to correspond to the activity modifier for an exercise currently being performed by the user. Over a duration of the workout, system 100 may use different ones of the activity modifiers to calculate calories burned using equation (1) corresponding to different exercises the user is prompted to perform. One or more factors may contribute to the activity modifier and/or adjustment of the modifier. Examples include, but are not limited to: pace, type of exercise, duration, and combinations thereof. Further, activity modifiers and/or variation of activity modifiers may be determined from predetermined values (such as a value assigned to an exercise or movement that a user is prompted to perform), the user's performance, information from a MET table on a particular exercise, and combinations thereof.

The completeness modifier may be used for adjusting the BMR based on how well a user's form corresponds to a desired form when performing an exercise. In an example, the completeness modifier may indicate what percentage of full movement was achieved for each repetition when performing an exercise (e.g., determine a percentage of a measured angle between the user's torso and thighs for a particular repetition of an exercise relative to a desired angle), or may be an average of the percentage of full movement for a predetermined number of repetitions (e.g., last three exercises, last five exercises, all exercises, etc.). The completeness modifier may have a default value. In one example embodiment, the default value may be 0.1. In a second embodiment, the default value may be 1.0. The default value may be any value, including 0.0. System 100 may update the completeness modifier over time based on how well the user's form conforms to a desired form. One or more factors may contribute to the activity modifier and/or adjustment of the modifier. Examples include, but are not limited to: pace, type of exercise, duration, and combinations thereof. Further, activity modifiers and/or variation of activity modifiers may be determined from predetermined values (such as a value assigned to an exercise or movement that a user is prompted to perform), the user's performance, and combinations thereof.

Equation (2), provided below, may be utilized in further embodiments.

$$\text{Calories burned} = BMR * (\text{Activity modifier}) * (\text{Completeness modifier}) * (\text{Multiply Modifier}) + (\text{Addition Modifier}) \quad \text{Equation (2)}$$

Values for BMR, Activity Modifier, and/or Completeness Modifier of Equation (2) may be determined in accordance with one or more embodiments described above in reference to Equation (1). In one embodiment, the value of the Multiply Modifier may be defined for each type of exercise. In one example embodiment, the default value may be 0.1. In a second embodiment, the default value may be 1.0. The default value may be any value, including 0.0. System 100 may update the Multiply Modifier during a workout to correspond to a type of exercise the user is prompted to perform. In certain embodiments, the Activity Modifier may be obtained (either partially or entirely) from empirical data.

In certain embodiments, the value of the Addition Modifier may be defined for each type of exercise. In one example embodiment, the default value may be 0.1. In a second embodiment, the default value may be 1.0. The default value may be any value, including 0.0. System 100 may update the Addition Modifier during a workout to correspond to a type of exercise the user is prompted to perform. In certain embodiments, the Activity Modifier may be obtained (either partially or entirely) from empirical data.

System 100 may calculate the calories burned over a duration of a workout, which may incorporate the utilization of equations (1) or (2). System 100 may cause the display 136 to display a running total of calories burned. In certain embodiments, the total may be determined for one or more completed repetitions and one or more completed sets of each exercise. System 100 may also calculate and cause display of calories burned by type of exercise performed. Other information such as, for example, peak/minimum/average calorie burning rate by workout, by repetition, by set, or by exercise type may also be calculated and displayed. System 100 may periodically determine an amount of calories burned by the user while exercising using equation (1). System 100 may indicate a current amount of calories burned that is continually updated over a workout (e.g., a running total), or may update the calories burned amount at predetermined times (e.g., user completes a set of a first type of exercise and begins a set of second type of exercise, at the end of the workout session, etc.). System 100 may also inform the user how many calories were burned during each repetition as well as in each set of an exercise.

One or more of the inputs and/or variables used in the determination of caloric expenditure (such as with equation (1)) may remain the same regardless of the type of exercise being performed by the user, yet others may vary. For example, the BMR may be the same over the entire workout as a user's weight, height, and age do not change appreciably over the course of a workout. Further, one or more of the Activity modifier, Completeness modifier, Multiply Modifier, and Addition Modifier may vary over the workout. The values (and/or variation) of the values may depend on the type exercise currently being performed by the user.

The Completeness modifier may vary from repetition to repetition. As noted above, system 100 may generate the Completeness modifier based on monitoring a user's form while they perform an exercise. Generally, an exercise includes a sequence of motions to perform one repetition, and a user typically performs a set that includes two or more repetitions. A user's form may vary from repetition to repetition, and so may the Completeness modifier.

System 100 may determine calories burned using equation (1) based on a Completeness modifier that varies from repetition to repetition, or based on a filtered version of the Completeness modifier. To filter the Completeness modifier, the system 100 may, for example, determine a Completeness modifier for one or more repetitions, may average some or all of the Completeness modifiers, and may use the average in equation (1). Also, system 100 may generate the Completeness modifier as a weighted average, where Completeness modifiers of some repetitions may be given greater weight than others. For example, system 100 may apply a decaying function where more recent Completeness modifiers are weighted more heavily than less recent when generating an average.

System 100 may also allow a user to make desired movements, and calculate an amount of calories burned for such movement. In one embodiment, all detected movements may be utilized in calculations. Yet in other embodiments, only certain (e.g., system supported and/or those prompted to be performed) movements may be considered. System 100 may process data from image capturing device 126 and/or from various sensors to attempt to classify a user's movement. For example, system 100 may compare the user's movement to other known movements for which a MET table has been defined. If a user's movement corresponds to a known movement for which a MET table has been defined, then system 100 may use the identified MET table for calculating an amount of calories burned.

If the user's movement does not match an exercise defined by a MET table, the system 100 may identify one or more exercises that include movements similar to the movement being performed by the user. For example, system 100 may determine that the user's lower body moves similar to a squat and upper body moves similar to a pushup. System 100 may calculate the number of calories the user would burn using the identified MET tables as if the users were doing a squat, and as if they were doing a pushup, as approximations for the amount of calories burned by the user. In further embodiments, a new entry may be created. In this regard, certain embodiments may permit the entry and later identification of new movements and/or exercises. In certain embodiments, the user may provide inputs regarding an approximate caloric expenditure for an unidentified movement/exercise. Yet in other embodiments, system 100 may calculate caloric expenditure, such as from one or more sensors as discussed herein. In still yet further embodiments, system 100 may utilize one or more sensor readings as well as an input from a user (and/or third-party) in determining attributes, such as caloric expenditure, for previously unknown movements or exercises. Examples of estimating caloric expenditure without MET tables, may include but are not limited to, determining changes in potential energy. Examples of using changes in potential energy are provided in the next section.

System 100 may be configured to transmit calories burned estimates to a social networking website. The users may be ranked based on their total number of calories burned for a desired time interval (e.g., rank by day, week, month, year, etc.). With reference again to FIG. 3, the method may end or may return to any of the preceding blocks.

i. Energy Expenditure Estimate based on Changes in Potential Energy

System 100 may also calculate an energy expenditure estimate of a user for physical activities not defined by a MET table. For example, system 100 may calculate an amount of calories burned by a user performing any desired combination of movements. During a workout, a user may be exposed to their own body weight and gravity. A location of a user's center of mass, or of a center of mass of a particular body part, may be utilized in estimating an amount of calories burned by the user performing an athletic activity.

Figure 8:
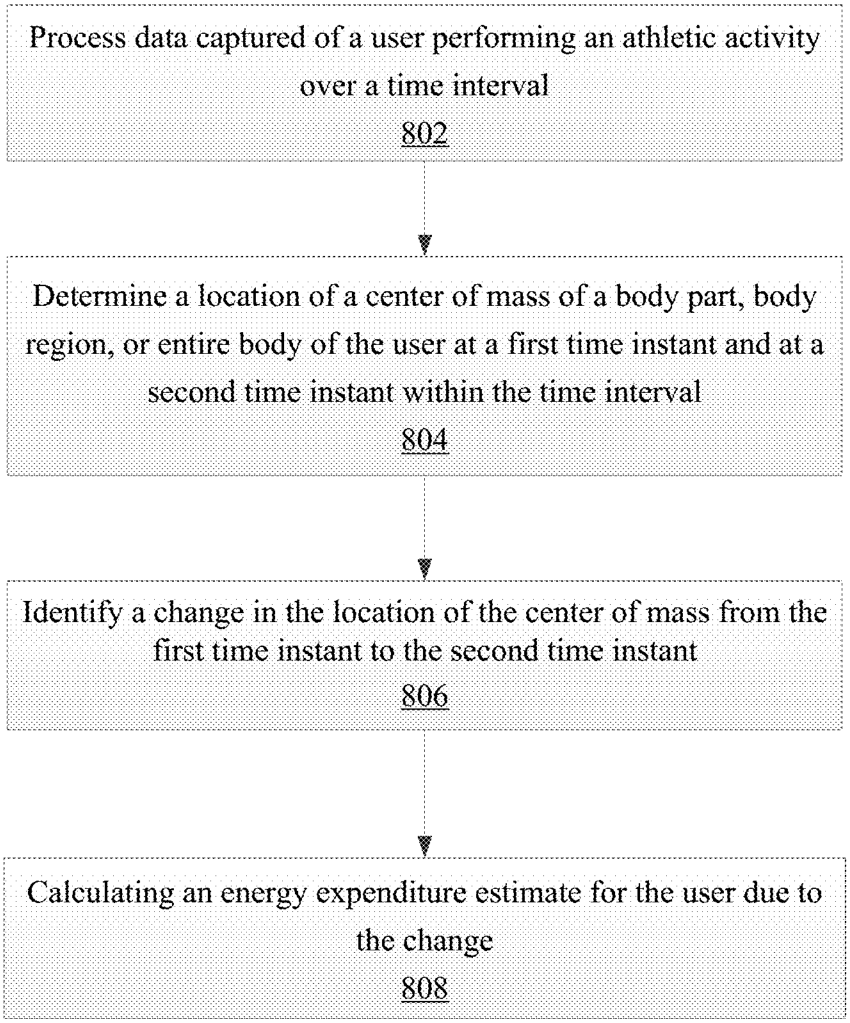
FIG. 8 illustrates an example flow diagram of a method for calculating an energy expenditure estimate for a user while performing an athletic activity based on monitoring changes in potential energy, in accordance with example embodiments.

FIG. 8 illustrates an example flow diagram of a method for calculating an energy expenditure estimate for a user while performing an athletic activity based on monitoring changes in potential energy, in accordance with example embodiments. The method may be implemented by a computer, such as, for example, computer 102, device 138, 140 and/or 142 as well as other apparatuses. The blocks shown in FIG. 8 may be rearranged, some blocks may be removed, additional blocks may be added, each block may be repeated one or more times, and the flow diagram may be repeated one or more times. The flow diagram may begin at block 802.

In block 802, various embodiments may involve processing data captured of a user performing an athletic activity over a time interval. In an example, system 100 may prompt a user to perform ten repetitions of a lunge and may process data captured of the user performing the lunge. The data may be video captured by the camera 126 or may be captured by the infrared transceiver 128, and/or by the other device sensors 138, 140, and 142.

Figure 9:
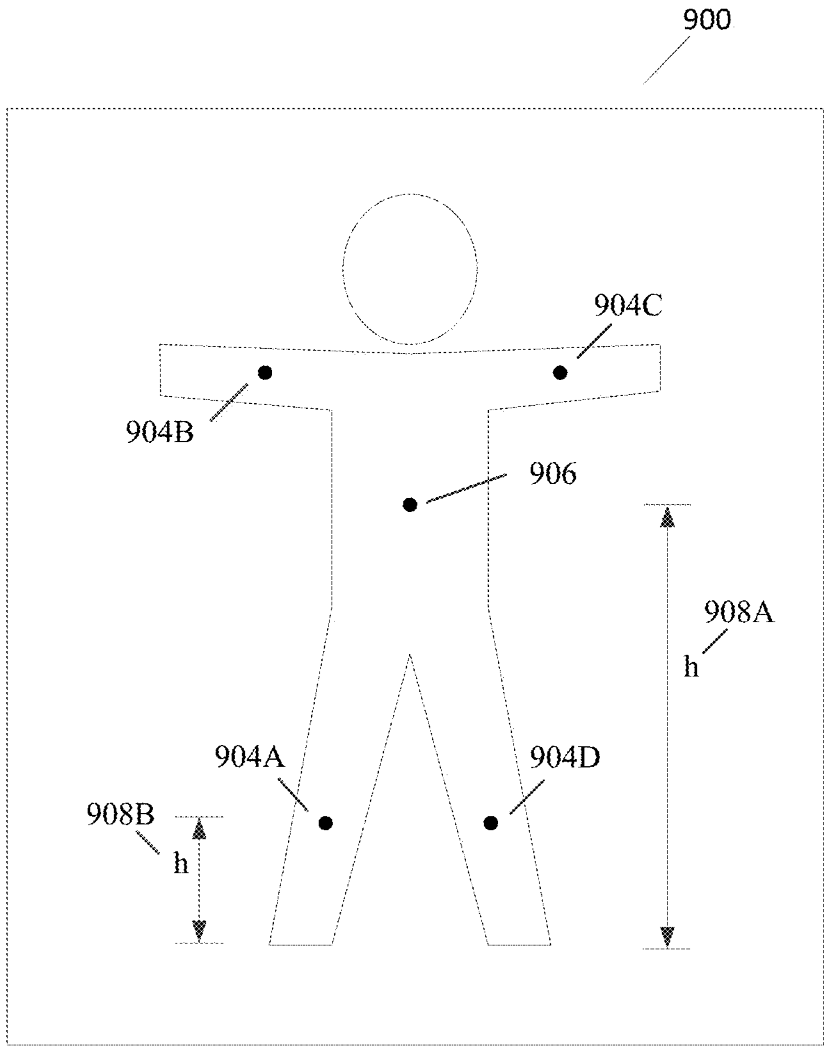
FIGS. 9, 10A-B, and 11 illustrate example locations of centers of mass for a virtual avatar of user, in accordance with example embodiments.

In block 804, various embodiments may involve determining a location of a center of mass of a body part, body region, or of an entire body of the user at a first time instant and at a second time instant within the time interval. Yet in other embodiments, a center of movement may be utilized. For simplicity purposes, however, a center of mass will be discussed. In an example, system 100 may instruct the user to place sensors at locations of corresponding to a center of mass for one or more body parts of the user. With reference to FIG. 9, one or more of center of mass locations may be at example locations 904A-D and 906, or at other locations on the user's body. Any number of locations may be monitored. At least one sensor may wirelessly transmit sensor data indicating a time and a location of the sensor (or location of a body part as detected by the sensor). A location may be coordinates in a coordinate system (e.g., Cartesian coordinate system) and may be associated with a time stamp indicating when the sensor was at a particular coordinate. In certain embodiments, system 100 may process the sensor data to periodically determine locations 904A-D and 906. For example, system 100 may receive sensor data, such as from device sensors 138, 140 and/or 142. Computer 102 (or another component of system 100) may process data as part of determining locations (such as locations 904A-D and 906). In one embodiment, data may be processed on a routine ongoing-basis, such as four times per second. In another example, computer 102 (or another component of system 100) may process data from image capturing device 126 to determine locations 904A-D and/or 906.

Figure 10B:
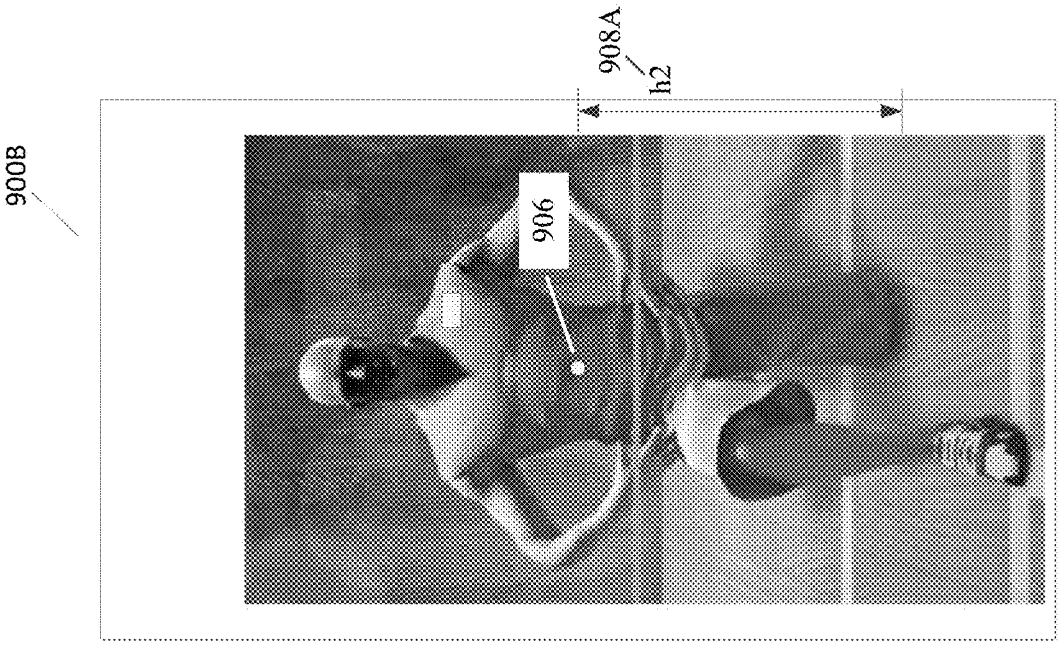
Figure 10A:
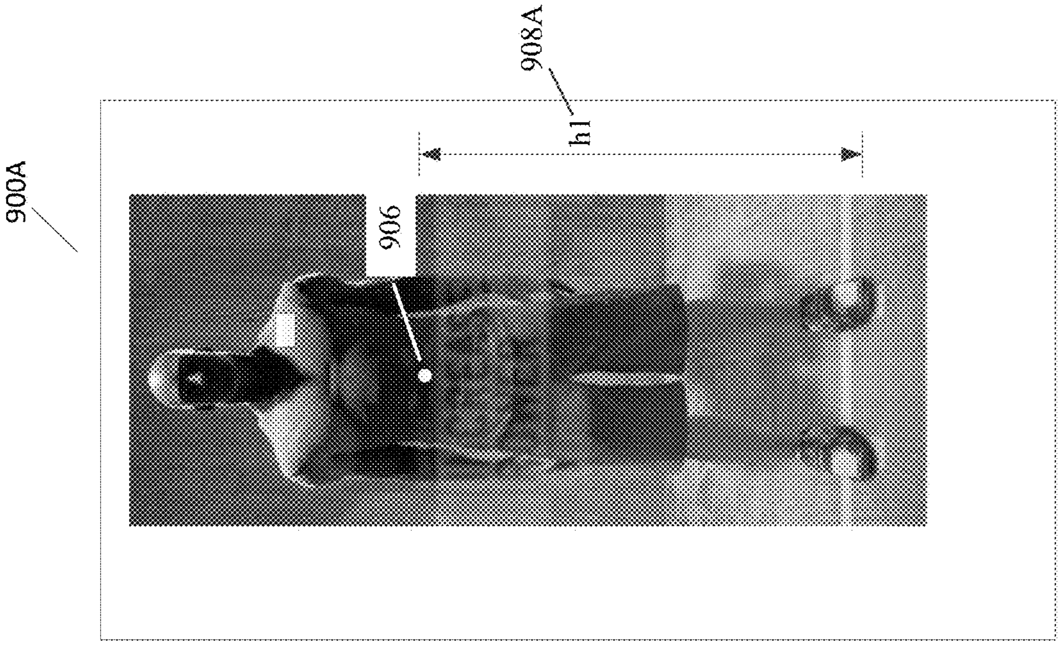
Figure 11:
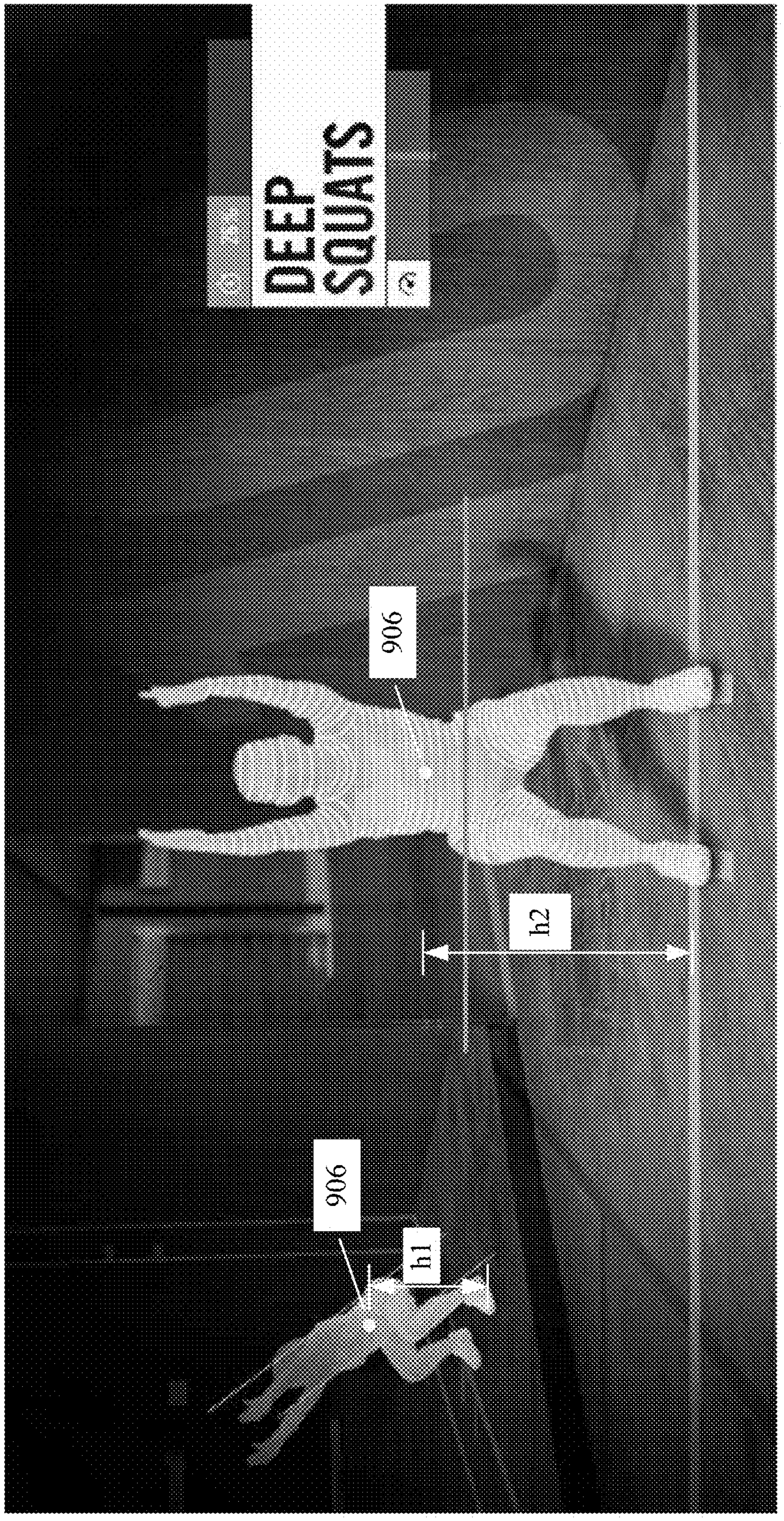

In block 806, various embodiments may involve identifying a change in the location of the center of mass from the first time instant to a second time instant. As discussed above, system 100 may determine locations 904A-D and 906 at one time and at a subsequent time. For example and with reference to FIGS. 10A-B, a user is shown performing a lunge. FIG. 10A corresponds to a first time instant and FIG. 10B corresponds to a second time instant. In FIG. 10A, a location 906 of a user's center of mass is at a height "h1" (designated by 908A) off of the ground. In FIG. 10B, a location 906 of a user's center of mass is at a height "h2" (designated by 908A) off of the ground. One or more components of system 100 may determine a difference between height "h1" and "h2" to determine a change in a location 906 of the center of mass. System 100 may also calculate changes to locations 904A-D of centers of mass for other body parts, or changes to other locations of body parts or body regions of the user. System 100 may also process video of a user taken from different angles, as shown in FIG. 11, to determine locations 904A-D and 906. For example, system 100 may determine height "h1" for location 906 in a perspective view and height "h2" for location 906 in a front view of the user. System 100 may average the different height measurements, or may use one or the other.

With reference again to FIG. 8, in block 808, various embodiments may calculate an energy expenditure estimate for the user due to the change. In an example, the physics concept of potential energy may be used to estimate the amount of work done by the user, and to calculate calories burned based on work.

In an example, one or more components of system 100 may determine changes of a location 906 from one time instant to another to determine an amount of work performed by the user. Potential Energy (PE)=m*g*h, where m=mass of the user (or body part), g=the acceleration due to gravity, and h=height above ground. Work (W)=−ΔPE, where Δ is represents a change in potential energy. Substituting m*g*h, Work (W)=−m*g*Δh. Based on the above example in FIGS. 10A-B, W=−m*g*(h1−h2). System 100 may determine an amount of calories burned as a function of work multiplied by physiology of human efficiency. System 100 may determine the amount of calories burned based on the amount of work and a physiology of human efficiency (PHE) scaling factor. The system 100 may determine the PHE scaling factor as a function of one or more of the user's heart rate, pressure sensor data, and other information input by the user (e.g., age, weight, etc.)

System 100 may keep and/or transmit a running total of calories burned between subsequent time instants and inform the user of a total amount of calories burned up to that point in an exercise session. For example, system 100 may determine a height h of location 906 at a certain frequency (e.g., 2 times per second), and may calculate calories burned based on a difference in calories burned between each determination of height h. The system 100 may also track a total number of calories burned over a predetermined time range covering one or more workouts. A time range may include a week, month, year, cumulative time since a user began working out, or other defined metrics. One or metrics may comprise default values, predefined values, user-selectable values, and/or user-defined values. For example, system 100 may inform the user of how many calories they have burned during a specified time period, such as a day, week, month, and/or year. System 100 may also maintain data on average number of calories burned per workout, average number of calories burned based on a type of workout, a greatest number of calories burned during a single workout or during a predetermined time interval (e.g., month where highest amount of calories was burned), or other types of data.

In another example, system 100 may determine calories burned by movement of a particular body part or by a collection of body parts. For instance, a user may desire to know how many calories were burned by movement of their right leg. Using the above relationship between work and potential energy, and with reference again to FIG. 9, system 100 may monitor changes in the location 904A of the center of mass of the user's right leg (e.g., height 908B) from one time instant to a different time instant to calculate work. System 100 may estimate the mass of the user's right leg based on the user's weight and proportions. System 100 may then determine an amount of calories burned as a function of work multiplied by physiology of human efficiency, as described above. During an exercise session, system 100 may display, such as through display 136, a running total of calories burned attributable to movement of the user's right leg. System 100 may similarly determine calories burned based on locations 904B-D for the other limbs of the user. During an exercise session, system 100 may display a running total of calories burned by a user's entire body, as well by each limb.

System 100 may also permit a user to review an exercise session to determine how many calories were burned at certain times. For example, an exercise may involve performing repetitive motions (e.g., pushups). System 100 may identify each repetition within a set (e.g., each pushup within a set of 10), as well as a number of calories burned during each repetition. Over a set, one or more components of system 100 may identify the repetition where the user burned a highest number of calories as well as a lowest number of calories. In further embodiments, system 100 may estimate an average number of calories. These are merely exemplary statistics and those skilled in the art will readily appreciate that other analysis may be conducted without departing from the scope of this disclosure.

If an exercise session involves different types of exercises, system 100 may rank the exercise types based on the amount of calories burned by type. For example, an exercise session may involve 3 different types of exercises (e.g., pushups, sit-ups, squats). After completing the exercise session, system 100 may determine how many calories were burned by each exercise type (e.g., 10 calories for pushups, 13 calories for sit-ups, and 18 calories for squats), and rank the exercise types based on the number of calories burned (e.g., first squats, second sit-ups, third pushups). In further embodiments, energy expenditure (e.g., a quantity of calories burned) may be ranked as percentage over an ideal value or range for an exercise or routine. For example, if perfectly performing an exercise would burn about 100 calories, a first user who burned 90 calories may be assigned a better ranking than second user who only burned 85 for the same exercise. The users could have different ideal values or ranges, thus the determinations may utilize the percentage of the detected and/or estimated values as a percentage for that user's ideal value. In further embodiments, a user who is closer to 100% of their ideal value may be ranked higher than users who have over 100% of the ideal quantity of calories burned. In this regard, a user who expends more energy than estimated or calculated for an activity (e.g., exercise) may indicate improper movements, inefficiency, increased likelihood of injury, and/or combinations thereof. In certain implementations, the method of FIG. 8 may then end, or may return to any of the preceding blocks and/or other processes.

System 100 may also determine calories expended from pre-recorded videos. For example, a user may upload video of a professional basketball player dunking a basketball to system 100. One or more components of system 100 may process the video to determine locations of a center of mass of the player, or of particular body parts, at various points in time, and determine the amount of calories expended during the physical activity (e.g., by the player during the dunk) using the work-based calorie determination, described above.

In various embodiments of the invention energy expenditure may be calculated with multiple sensors. Some of the calculation may be independent of other calculations. For example, a user may perform an exercise while wearing a wrist worn sensor and while being observed by a camera based sensor system. The wrist worn sensor and the camera based system may independently calculate energy expenditure values. When two or more independent systems are utilized, different energy expenditure values may be calculated.

In some embodiments of the invention energy expenditure values are used to award points to users. When multiple sensors or systems of sensors are used to independently calculate energy expenditure, users may receive points for each sensor or system of sensors that calculates energy expenditure. Alternative, one energy expenditure value may be determined based on one of calculated values or some combination of the calculated values. For example, prior to beginning an exercise a user may select the sensor or sensor systems that will be used to calculate energy expenditure. Alternatively, a system may select the sensor or sensor system that will be used. The selection may be based on the accuracy in calculating energy expenditure for all of the available sensors or sensor systems. The selection and accuracy may be functions of the exercise that will be performed. For example, a first sensor may result in more accurate energy expenditure calculations while a user is running and a second sensor may result in more accurate energy expenditure calculations while a user is performing squats. Other embodiments may include using an average, a weighted average or a statistical solution to determine energy expenditure.

In addition to using multiple independent sensors and sensor systems for calculating energy expenditure, some embodiments of the invention may utilize multiple display devices for displaying energy expenditure or energy expenditure point values. When one sensor or sensor system is used to calculate energy expenditure, the display device associated with the sensor or sensor system that is not used may be disabled. Alternative, the display device associated with the sensor or sensor system that is not used may be driven by the sensor or sensor system that is used. For example, a wrist worn sensor system and a camera based system may both include displays for displaying energy expenditure. When both systems are available and the camera based system is selected to calculate energy expenditure, the camera based system may provide data to the wrist worn sensor system so that the display associated with the wrist worn sensor system displays the same values as the display associated with the camera based system. Similarly, when combinations of multiple independent sensor or sensor systems are used to calculate energy expenditure, the displays associated with each sensor or sensor system may be driven to display the same data.

II. Illustrative Methods for Combining Energy Expenditure Estimates

A. Illustrative Networks

Figure 12:
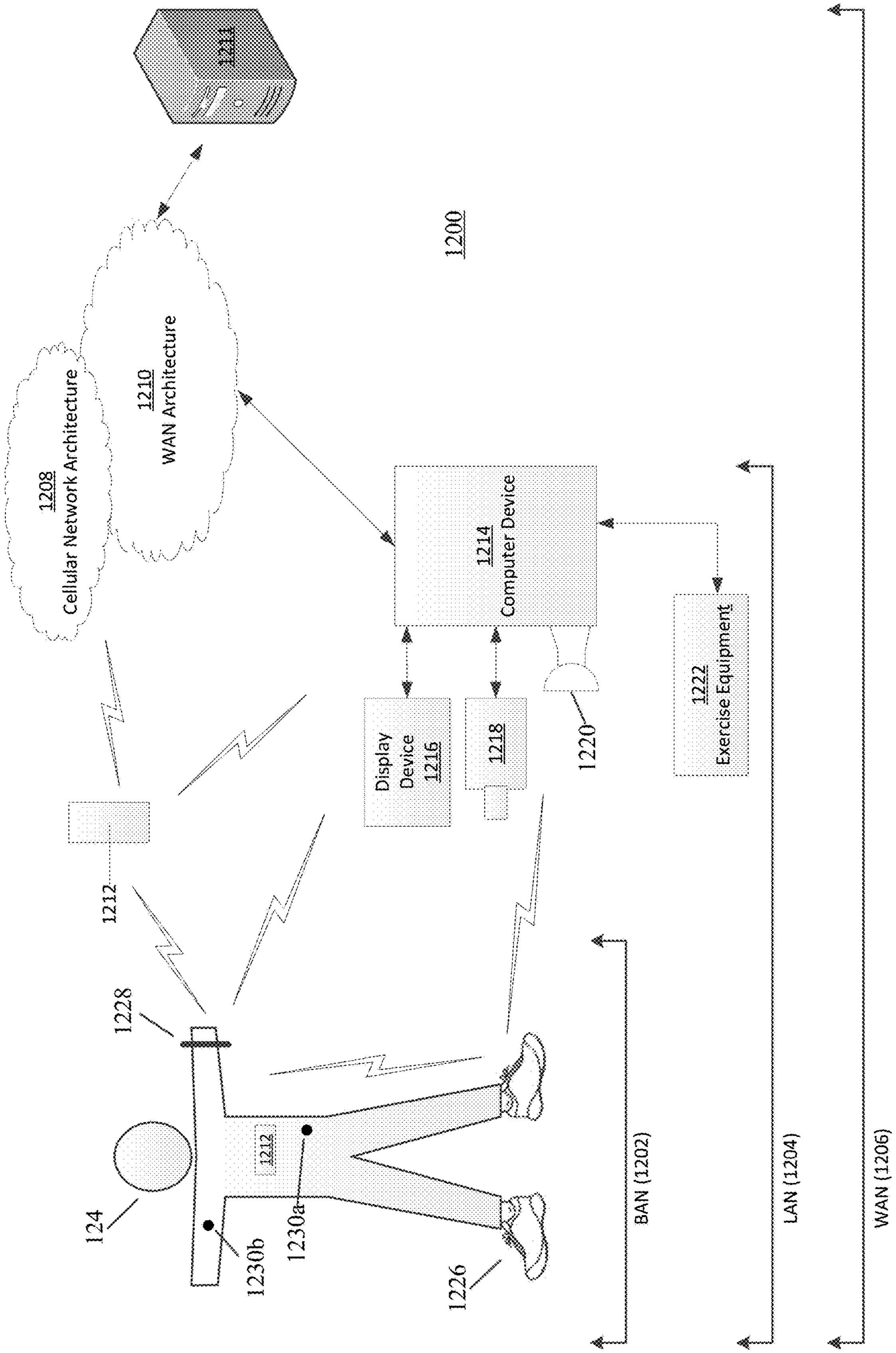
FIG. 12 illustrates an example of a system for determining a total energy expenditure of a user over a specified duration.

Aspects of this disclosure relate to systems and methods that may be utilized across a plurality of networks. In this regard, certain embodiments may be configured to adapt to dynamic network environments. Further embodiments may be operable in differing discrete network environments. FIG. 12 illustrates an example of a personal training system 1200 (e.g., system 100 of FIG. 1) in accordance with illustrative embodiments. Example system 1200 may include one or more interconnected networks, such as the illustrative body area network (BAN) 1202, local area network (LAN) 1204, and wide area network (WAN) 1206. As shown in FIG. 12 one or more networks (e.g., BAN 1202, LAN 1204, and/or WAN 1206), may overlap or otherwise be inclusive of each other. Those skilled in the art will appreciate that the illustrative networks 1202-1206 are logical networks that may each comprise one or more different communication protocols and/or network architectures and yet may be configured to have gateways to each other or other networks. For example, each of BAN 1202, LAN 1204 and/or WAN 1206 may be operatively connected to the same physical network architecture, such as cellular network architecture 1208 and/or WAN architecture 1210. For example, portable electronic device 1212 (e.g., device 138), which may be considered a component of both BAN 102 and LAN 104, may comprise a network adapter or network interface card (NIC) configured to translate data and control signals into and from network messages according to one or more communication protocols, such as the Transmission Control Protocol (TCP), the Internet Protocol (IP), and the User Datagram Protocol (UDP) through one or more of architectures 1208 and/or 1210. These protocols are well known in the art, and thus will not be discussed here in more detail.

Network architectures 1208 and 1210 may include one or more information distribution network(s), of any type(s) or topology(s), alone or in combination(s), such as for example, cable, fiber, satellite, telephone, cellular, wireless, etc. and as such, may be variously configured such as having one or more wired or wireless communication channels (including but not limited to: WiFi®, Bluetooth®, Near-Field Communication (NFC) and/or ANT technologies). Thus, any device within a network of FIG. 12, (such as portable electronic device 1212 or any other device described herein) may be considered inclusive to one or more of the different logical networks 1202-1206. With the foregoing in mind, example components of an illustrative BAN and LAN (which may be coupled to WAN 1206) will be described.

1. Example Local Area Network

LAN 1204 may include one or more electronic devices, such as for example, computer device 1214, such as the computer device 102 discussed above in reference to FIG. 1A. Computer device 1214, or any other component of system 1200, may comprise a mobile terminal, such as a telephone, music player, tablet, netbook or any portable device. In other embodiments, computer device 1214 may comprise a media player or recorder, desktop computer, server(s), a gaming console, such as for example, a Microsoft® XBOX, Sony® Playstation, and/or a Nintendo® Wii gaming console. Those skilled in the art will appreciate that these are merely example of devices for descriptive purposes and this disclosure is not limited to any console or computing device.

Those skilled in the art will appreciate that the design and structure of computer device 1214 may vary depending on several factors, such as its intended purpose. One illustrative implementation of computer device 1214 is discussed above in reference to FIG. 1B. In some cases, the system of FIG. 1B may be applicable to any device disclosed herein. In some cases, the computer device 1214 (e.g., the computer device 102) may include one or more processors, such as processor unit 106. In some cases, two or more processors may communicate with each other or other components via an interconnection network or bus. The processor unit 106 may include one or more processing cores, which may be implemented on a single integrated circuit (IC) chip. In some cases, the cores may include a shared cache and/or a private cache. One or more caches may locally cache data stored in a system memory (e.g., system memory 108), for faster access by components of the processor unit 106. The system memory 108 may be in communication with one or more processors via a chipset. The cache may be part of system memory 108 in certain embodiments.

In some cases, the computing system may include one or more I/O devices (e.g., input devices 120, output devices 122, etc.). I/O data from one or more I/O devices 120, 122 may be stored at one or more caches and/or system memory 108. Each of I/O devices 120, 122 may be permanently or temporarily configured to be in operative communication with a component of system 100 using any physical or wireless communication protocol via a communication circuit. In some cases, the communication circuit may include a chipset associated with one or more communication protocols, and/or may include one or more discrete components.

Returning to FIG. 12, four example I/O devices, shown as elements 1216-1222, are shown as being in communication with computer device 1214. Those skilled in the art will appreciate that one or more of devices 1216-1222 may be stand-alone devices or may be associated with another device besides computer device 1214. For example, one or more I/O devices may be associated with or interact with a component of BAN 1202, LAN 1204, and/or WAN 1206. I/O devices 1216-1222 may include, but are not limited to athletic data acquisition units, such as for example, sensors (e.g., image-capturing device 126 and/or sensor 128). In further embodiments, I/O devices 1216-1222 may be used to provide an output (e.g., audible, visual, or tactile cue) and/or receive an input, such as a user input from athlete 124. Example uses for these illustrative I/O devices are provided below, however, those skilled in the art will appreciate that such discussions are merely descriptive of some of the many options within the scope of this disclosure. Further, reference to any data acquisition unit, I/O device, or sensor is to be interpreted disclosing an embodiment that may have one or more I/O device, data acquisition unit, and/or sensor disclosed herein or known in the art (either individually or in combination).

Information from one or more devices (across one or more networks) may be used to provide (or be utilized in the formation of) a variety of different parameters, metrics or physiological characteristics including but not limited to: motion parameters, such as speed, acceleration, distance, steps taken, direction, relative movement of certain body portions or objects to others, or other motion parameters which may be expressed as angular rates, rectilinear rates or combinations thereof, physiological parameters, such as calories, heart rate, sweat detection, effort, oxygen consumed, oxygen kinetics, and other metrics which may fall within one or more categories, such as: pressure, impact forces, information regarding the athlete, such as height, weight, age, demographic information and combinations thereof.

System 1200 may be configured to transmit and/or receive athletic data, including the parameters, metrics, or physiological characteristics collected within system 1200 or otherwise provided to system 1200. As one example, WAN 1206 may include a server 1211. The server 1211 may have one or more components illustrated in FIG. 1B. Server 1211 may be configured to store computer-executable instructions on a non-transitory computer-readable medium. The instructions may comprise athletic data, such as raw or processed data collected within system 1200. System 1200 may be configured to transmit data, such as energy expenditure points, to a social networking website or host such a site. Server 1211 may be utilized to permit one or more users to access and/or compare athletic data. As such, server 1211 may be configured to transmit and/or receive notifications based upon athletic data or other information.

Returning to LAN 104, computer device 1214 is shown in operative communication with a display device 1216 (e.g., display device 136), an image-capturing device 1218 (e.g., image capturing device 126), sensor 1220 (e.g., sensor 128) and/or exercise device 1222. In one embodiment, display device 1216 may provide audio-visual cues to athlete 124 to perform a specific athletic movement. The audio-visual cues may be provided in response to computer-executable instruction executed on computer device 114 or any other device, including a device of BAN 102 and/or WAN. In one embodiment, data may be obtained from image-capturing device 1218 and/or other sensors, such as sensor 1220, which may be used to detect (and/or measure) athletic parameters, either alone or in combination with other devices, or stored information, as discussed above.

Element 1230 of FIG. 12 shows an example sensory location (e.g., sensory location 144) which may be associated with a physical apparatus, such as a sensor, data acquisition unit, or other device. Yet in other embodiments, it may be a specific location of a body portion or region that is monitored, such as via an image capturing device (e.g., image capturing device 1218). In certain embodiments, element 1230 may comprise a sensor, such that elements 1230*a* and 1230*b* may be sensors integrated into apparel, such as athletic clothing. Such sensors may be placed at any desired location of the body of user 124. Sensors 1230*a/b* may communicate (e.g., wirelessly) with one or more devices (including other sensors) of BAN 1202, LAN 1204, and/or WAN 1206.

In one embodiment, exercise device 1222 may be any device configurable to permit or facilitate the athlete 124 performing a physical movement, such as for example a treadmill, step machine, etc. There is no requirement that the device be stationary. In this regard, wireless technologies permit portable devices to be utilized, thus a bicycle or other mobile exercising device may be utilized in accordance with certain embodiments. Those skilled in the art will appreciate that equipment 1222 may be or comprise an interface for receiving an electronic device containing athletic data performed remotely from computer device 1214. For example, a user may use a sporting device (described below in relation to BAN 1202) and upon returning home or the location of equipment 1222, download athletic data into element 1222 or any other device of system 1200. Any I/O device disclosed herein may be configured to receive activity data.

2. Body Area Network

BAN 1202 may include two or more devices configured to receive, transmit, or otherwise facilitate the collection of athletic data (including passive devices). Exemplary devices may include one or more data acquisition units, sensors, or devices known in the art or disclosed herein, including but not limited to I/O devices 116-122. Two or more components of BAN 102 may communicate directly, yet in other embodiments, communication may be conducted via a third device, which may be part of BAN 102, LAN 104, and/or WAN 106. One or more components of LAN 104 or WAN 106 may form part of BAN 102. In certain implementations, whether a device, such as portable device 112, is part of BAN 102, LAN 104, and/or WAN 106, may depend on the athlete's proximity to an access point to permit communication with mobile cellular network architecture 108 and/or WAN architecture 110. User activity and/or preference may also influence whether one or more components are utilized as part of BAN 102. Example embodiments are provided below.

User 124 may be associated with (e.g., possess, carry, wear, and/or interact with) any number of devices, such as portable device 112, shoe-mounted device 126, wrist-worn device 128 and/or a sensing location, such as sensing location 130, which may comprise a physical device or a location that is used to collect information. One or more devices 112, 126, 128, and/or 130 may not be specially designed for fitness or athletic purposes. Indeed, aspects of this disclosure relate to utilizing data from a plurality of devices, some of which are not fitness devices, to collect, detect, and/or measure athletic data. In certain embodiments, one or more devices of BAN 102 (or any other network) may comprise a fitness or sporting device that is specifically designed for a particular sporting use. As used herein, the term "sporting device" includes any physical object that may be used or implicated during a specific sport or fitness activity. Exemplary sporting devices may include, but are not limited to: golf balls, basketballs, baseballs, soccer balls, footballs, powerballs, hockey pucks, weights, bats, clubs, sticks, paddles, mats, and combinations thereof. In further embodiments, exemplary fitness devices may include objects within a sporting environment where a specific sport occurs, including the environment itself, such as a goal net, hoop, backboard, portions of a field, such as a midline, outer boundary marker, base, and combinations thereof.

In this regard, those skilled in the art will appreciate that one or more sporting devices may also be part of (or form) a structure and vice-versa, a structure may comprise one or more sporting devices or be configured to interact with a sporting device. For example, a first structure may comprise a basketball hoop and a backboard, which may be removable and replaced with a goal post. In this regard, one or more sporting devices may comprise one or more sensors, such as one or more of the sensors discussed above in relation to FIGS. 1-3, that may provide information utilized, either independently or in conjunction with other sensors, such as one or more sensors associated with one or more structures. For example, a backboard may comprise a first sensor configured to measure a force and a direction of the force by a basketball upon the backboard and the hoop may comprise a second sensor to detect a force. Similarly, a golf club may comprise a first sensor configured to detect grip attributes on the shaft and a second sensor configured to measure impact with a golf ball.

Looking to the illustrative portable device 1212, it may be a multi-purpose electronic device, as discussed above in reference to portable device 138 of FIG. 1. The portable device 1212 may include a telephone and/or a digital music player, as discussed above. As known in the art, digital media players can serve as an output device, input device, and/or storage device for a computer. Device 1212 may be configured as an input device for receiving raw or processed data collected from one or more devices in BAN 1202, LAN 1204, or WAN 1206. In one or more embodiments, portable device 1212 may comprise one or more components of computer device 1214. For example, portable device 1212 may be include a display 1216, image-capturing device 1218, and/or one or more data acquisition devices, such as any of the I/O devices 1216-1222 discussed above, with or without additional components, so as to comprise a mobile terminal.

B. Managing Energy Expenditure Estimates from Multiple User Devices

Figure 13A:
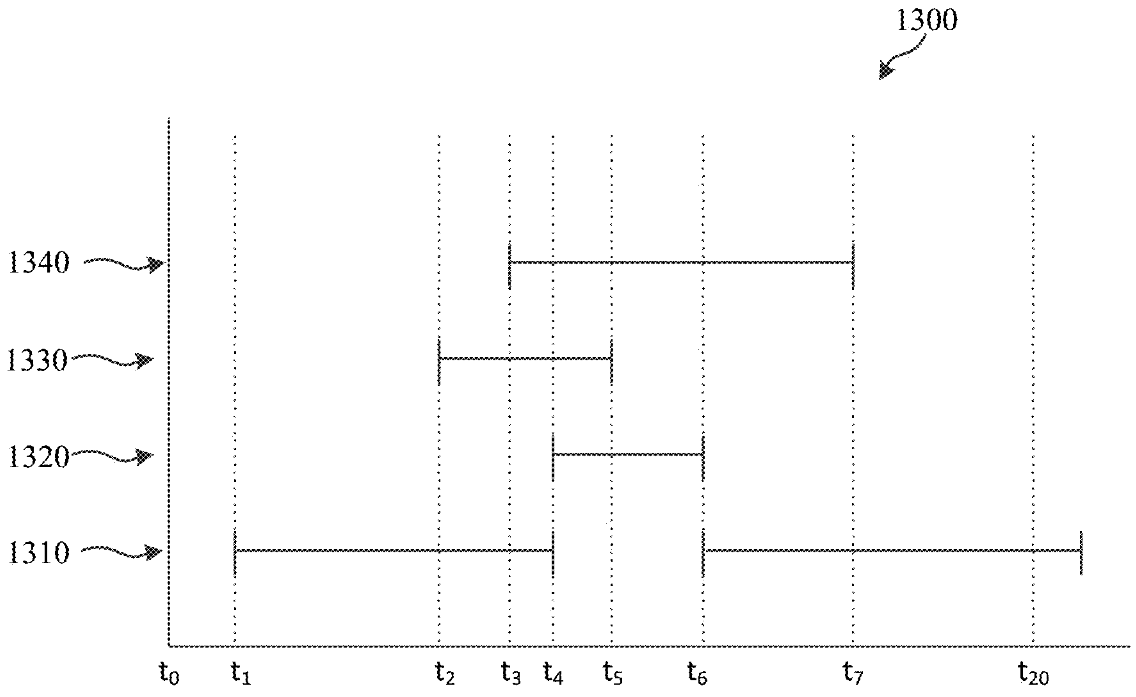
FIGS. 13A-B show illustrative charts showing use of two or more devices capable of monitoring energy expenditure of a user while performing one or more athletic activities and/or exercises.
Figure 13B:
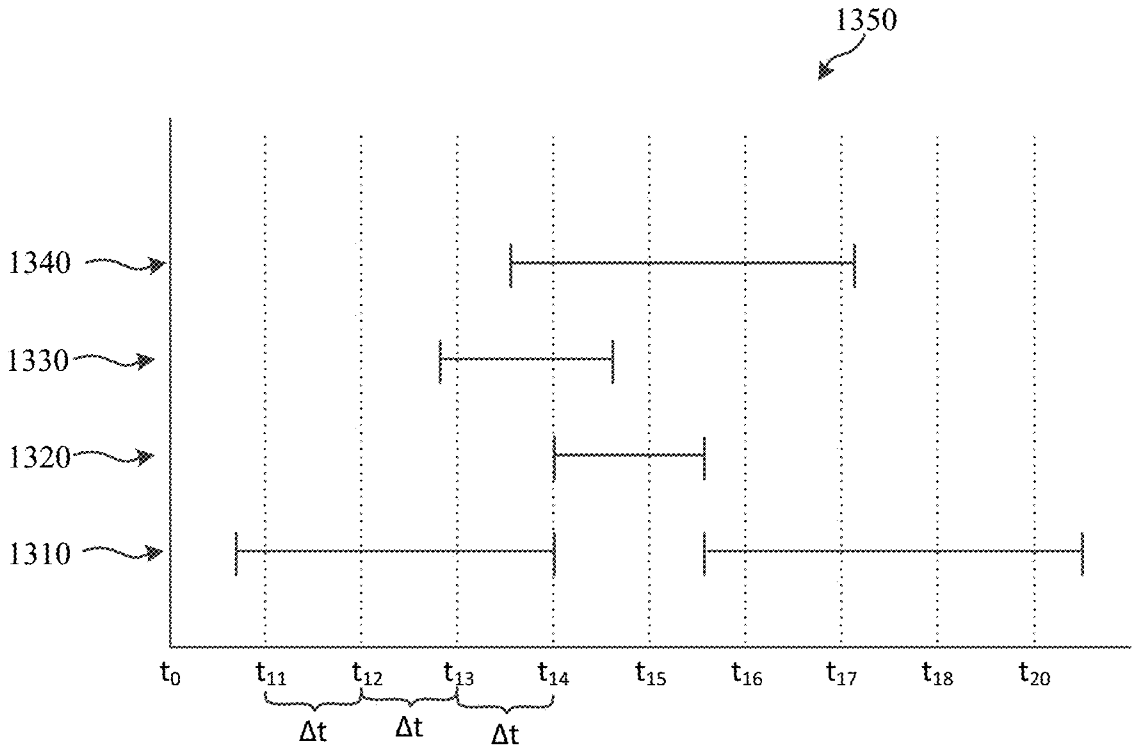

In some cases, as shown in FIGS. 13A-B, the user 124 may own and/or use multiple athletic activity monitoring devices to monitor one or more metrics, such as energy expenditure, heart rate, pace, distance, among others, during athletic activity performed over a specified duration. (e.g., an hour, a day, a week, a month, etc.), such as duration $t_0$-$t_{20}$. For example, the user 124 may own and/or use one or more wrist-worn devices 142, 1228, one or more shoe-mounted devices 140, 1226, one or more computer devices (e.g., portable device 138, 1212, computer device 102, 1214, server 134, 1211, etc.) and/or one or more sporting devices, such as equipment 1222. Over time, the user 124 may desire to use one or more of these devices individually, or in combination. For example, the user may perform an exercise (e.g., running, basketball, etc.) using the wrist-worn device 142, 1228 and the shoe-mounted device 140, 1226. In another illustrative example, the user 124 may additionally use the one or more computing devices to further monitor any athletic activities performed, in combination with the wrist-worn device 142, 1228 and/or the shoe-mounted device 140, 1226.

Sometimes, the user 124 may desire to use one or more of the above-mentioned or other athletic activity monitoring devices individually. Other times, the user 124 may use the athletic activity monitoring devices in some combination. For example, the user 124 may make the decision about which of the one or more athletic activity monitoring devices to use based upon an exercise type and/or an activity to be performed. In an illustrative example, the user 124 may use a first wrist-worn device 124, 128 when performing a first activity (e.g., walking, tennis, swimming, etc.) and a second wrist-worn device 124, 1228 for a second activity (e.g., running, biking, etc.). The user 124 may base the decision of which device to use based on one or more factors, including, but not limited to, a feature set associated with either the first or second wrist-worn devices 142, 1228. For example, the second wrist-worn device 142, 1228 may include features not available to and/or implemented in the first wrist-worn device 142, 1228, such as an interface to a global positioning system and/or a health monitoring device (e.g., a heart rate monitor, an oxygen sensor, etc.).

In an illustrative embodiment, one or more of the athletic activity monitoring devices (e.g., wrist-worn device 142, 1228, shoe-mounted device 140, 1226, portable device 138, 1212, computer device 102, 1214, server 134, 1211, equipment 1222, etc.), may include at least one processor, a sensor, a communication circuit, a display and/or other circuits for monitoring and/or communicating information about exercises performed by the user 124. In some cases, the communication circuit may be configured to communicate at least energy expenditure information over a network, such as the BAN 1202, the LAN 1204 and/or the WAN 1206. For example, the communication circuit may be configured to communicate, via a wired and/or a wireless link, between the apparatus and at least a second device. In some cases, the energy expenditure information may include at least a first energy expenditure estimate corresponding to a first exercise monitored by the first sensor during a first time frame and a second energy expenditure estimate corresponding to a second exercise monitored by one or more different devices during a second time frame.

One or more of the athletic activity monitoring devices may be configured to obtain motion data from movements performed by the user 124 and determine an energy expenditure estimate of the user 124 corresponding to the monitored first exercise, as discussed above. In some cases, a device, such as equipment 1222, may communicate activity information about the user to a different device (e.g., the computer 1214, the portable device 1212, the wrist-worn device 1228, and/or the shoe-mounted device 1226), such that a different device than the device collecting the motion computes at least a portion of the energy expenditure estimate based on the information received from the equipment 1222. After the energy expenditure estimate is determined, some and/or all energy expenditure estimate determined by the one or more different athletic activity monitoring devices may be communicated over one or more of the BAN 1202, the LAN 1204, and the WAN 1206. For example, the system 1200 may be configured to synchronize different energy expenditure estimates (e.g., a first energy expenditure estimate determined by the wrist-worn device 1228, a second energy expenditure estimate determined by the shoe-mounted device 1226, a third energy expenditure estimate determined by the computer device 1228, etc.) between the two or more different devices associated with a particular user 1284.

FIG. 13 shows a chart illustrating the collection of motion data from two or more sensors over a duration of time (t). Specifically, FIG. 13A shows chart 1300 that illustrates the collection and/or synchronization of motion data in relation to activities performed by the user 124 and FIG. 13B shows chart 1350 that illustrates the collection and/or a more regularly scheduled synchronization of motion data in relation to a specified time interval. In some cases, such as during various time intervals between $t_1$ and $t_7$, two or more devices 1310-1340 may be used to monitor a same exercise. In some cases, one or more or the devices 1310-1340 may include sensors and/or algorithms that may be configured to provide more accurate and/or detailed metrics corresponding to a particular activity performed by the user 124. For example, the user 124 may use a general-purpose energy tracker (e.g., a first device 1310) to generally monitor activities performed during the day. In some cases, however, the user 124 may desire a more accurate and/or detailed metrics when performing a particular exercise, such as during athletic training. Here, the user 124 may remove the first device 1310 (e.g., a wrist-worn general purpose energy tracking device) and use a second device 1310 having features configured for monitoring a particular athletic activity. In some cases, the user 124 may desire to use two or more of the devices 1310-1340 when monitoring a particular athletic activity. In such cases, one or more of the devices may be configured to provide more detailed metrics about at least a portion of the athletic activity to be performed by the user 124. For example, a shoe-mounted device 140, 1226 may be configured to provide information (e.g., force metrics) that may be combined with acceleration and/or distance metrics provided by sensors in a wrist-worn device 142, 1228. The devices 1310-1340 may be configured to synchronize obtained over a time period and to combine the synchronized metrics to provide a more accurate and/or detailed assessment of the athletic activities performed by the user 124.

In one embodiment, at least two sensors configured to collect motion data may be located on separate devices. As mentioned above, the user 124 may desire to use different combinations of the one or more devices over a particular duration (e.g., a day). Each individual device may be configured to determine an energy expenditure estimate corresponding to an amount of energy expended by the user 124 while using that particular device. However, the user 124 may desire to view the user's total energy expenditure estimate for all exercises and/or athletic activities performed, for example, over a course of a day, on each of the different devices. This may be especially advantageous when one or more sensors are stationary and/or difficult to possess or otherwise use throughout the day. For example, a camera-based sensor may be associated with a console or stationary computing device, and as such, may not be utilized to track the user's 124 all-day activity. Likewise, certain all-day activity trackers may accurately detect or measure most activities, however, are not as accurate as other sensors and/or devices for specific motions and/or activities that user 124 engages in. Sometimes, different devices may be configured to synchronize, such as via the BAN, LAN, and/or WAN to a computing device (e.g., server 1211). In some cases, the server 1211 may be configured to determine the total energy expenditure estimate for the user 124 when each device has synchronized energy expenditure information with the server 1211. To view this total energy expenditure estimate, the user 124 may log into the server 1211 using one or more devices, such as the portable device 1212 and/or the computing device 1214. However, in some cases, logging into the server 1211 over the WAN may be inconvenient for the user. For these times, and others, it may be desired for at least some of the athletic activity monitoring devices to compute and/or display the total energy expenditure information of the user for a particular time period.

In some cases, two or more of the computer 1214, the portable device 1212, the wrist-worn device 1228, and/or the shoe-mounted device 1226 and the exercise equipment 1222 may be configured to exchange, or otherwise communicate, information about exercises performed by the user 124. In some cases, the information may include, but not be limited to, energy expenditure estimates, activity start times and/or end times, device usage start times and/or end times, system clock information, sensor information (e.g., a force, a velocity, an acceleration, gyroscopic information, etc.), and/or an activity type. The athletic activity monitoring devices may be configured to automatically synchronize (e.g., communicate) the information, such as at the expiration of a specified time interval (e.g., 10 minutes, 15 minutes, 1 hour, etc.), at a start and/or end time associated with use of a device, and/or at a start and/or end time associated with a particular exercise. In other cases, the user 124 may trigger, or otherwise begin, a synchronization process, such as by using an input of one or more of the devices.

The charts 1300 and 1350 show illustrative use of multiple sensors, wherein at least two sensors are associated with different devices, over a particular duration, $t_0$-$t_{20}$ (e.g., 24 hours). In these illustrative examples, the user 124 may use multiple devices 1310-1340, such as over a course of a time duration, e.g., a day. For example, the devices may include a first wrist-worn device 1310, a second wrist-worn device 1320, a shoe-mounted device 1330 and a computer device 1340. In some cases, the user 124 may use two or more devices serially, such as the first wrist-worn device 1310, such as between times $t_1$ and $t_4$, and $t_6$ and $t_{20}$ and the second wrist-worn device 1320, such as between times $t_4$, and $t_6$. For example, the user may wear the first wrist-worn device 1310 for monitoring one or more activities over the course of a day. In some cases, however, the user 124 may desire to use the second wrist-worn device 1320. For example, the user 124 may desire to wear a GPS enabled device during a run and/or bicycle ride or a water-proof device during a swim, to name two examples. In other cases, two or more of the devices 1310-1340 may be used simultaneously. For example, the shoe-worn device 1330 and/or the computer device 1340 may be used in parallel with one or more of the other devices 1320-1340. For example, the shoe-worn device 1330 may be used simultaneously with the first wrist-worn device 1310 from $t_2$-$t_3$, the second wrist-worn device from $t_4$-$t_5$, and the computer device from $t_3$-$t_5$. Similarly, the computer device 1340 may be used with the first wrist worn device 1310 from $t_3$-$t_4$ and $t_6$-$t_7$ and with the shoe-worn device 1330 from $t_3$-$t_5$.

During use, each of the different devices 1310-1340 may be configured to communicate, by a communication circuit and one or more communication networks 1202-1206, energy expenditure information between the different devices 1310-1340. For example, the energy expenditure information communicated by the devices 1310-1340 may include at least a first energy expenditure estimate determined from a sensor located on a first device and a second energy expenditure estimate determined from a sensor on a second device. The sensor data may be processed on the device comprising the sensor collecting the data and/or a remote device. As mentioned above, in some cases, the devices 1310-1340 may be configured to communicate energy expenditure information at specified times. For example, the devices 1310-1340 may be configured to synchronize energy expenditure information at a start of a monitored duration (e.g., time $t_0$) and/or at an end of a monitored duration (e.g., time $t_{20}$). In some cases, the devices 1310-130 may be configured to synchronize energy expenditure information at the start time (e.g., $t_1$, $t_2$, $t_3$, $t_4$, $t_6$) and/or the end time (e.g., $t_4$, $t_5$, $t_6$, $t_7$) associated with use of the devices 1310-1340. In some cases, the synchronization times may correspond to one or more exercises performed during use of the devices 1310-1340, which may or may not correspond to the usage time of the devices 1310-1340. For example, a particular exercise may be monitored by use of two or more of the devices 1310-1340, where the exercise may continue after one of the devices is no longer used. In other cases, an indication that the exercise has ended may be determined from the motion data showing that the user 124 is no longer actively using one or more of the devices 1310-1340. In some cases, as shown in chart 1350, one or more devices (e.g., devices 1310-1340) may be configured to synchronize, or otherwise communicate, energy expenditure information after a specified time interval Δt has elapsed (e.g., at regular time intervals during the duration $t_0$-$t_{20}$). In some cases, one or more of devices 1310-1340 may include a system clock that may be used at least for associating time information to monitored and determined energy expenditure information. The system time kept by the system clock may be used during normal operation of the devices 1310-1340 and/or during synchronization. In some cases, one or more of the devices 1310-1340 may be configured to synchronize or otherwise set each clock to a similar time as part of the synchronization process and/or to facilitate the synchronization process.

Figure 14A:
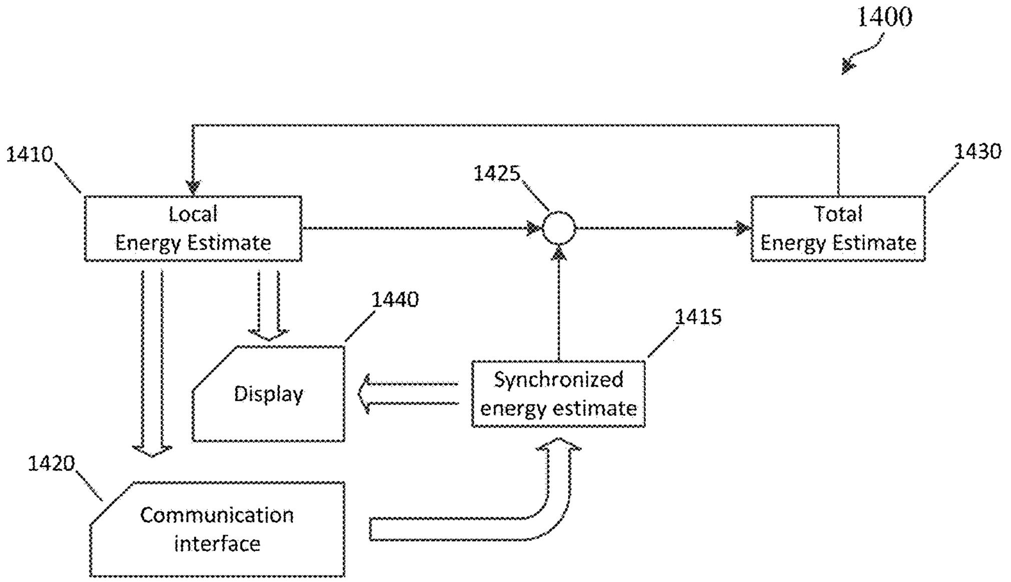
FIGS. 14A-B show illustrative block diagram representations of at least a portion of a device 1400, 1450 for determining and/or displaying energy expenditure estimates.
Figure 14B:
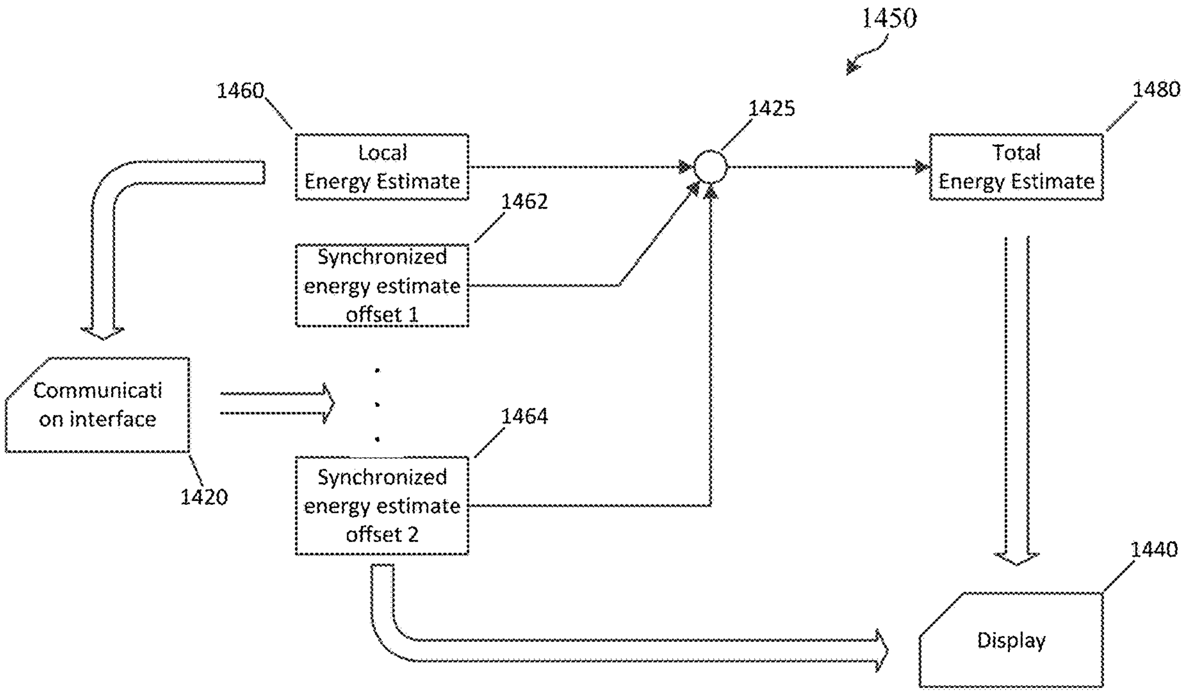

FIGS. 14A-B show illustrative block diagram representations of at least a portion of a device 1400, 1450, respectively for determining and/or outputting energy expenditure estimates. As discussed above, the devices 1400, 1450 may include a display 1440 configured for displaying one or more energy expenditure values to a user 124. Also, the device 1400, 1450 may be configured to determine an energy expenditure estimate for motions performed by a user. In certain embodiments, the same device comprises the sensor utilized to capture the motion data. During a specified time period, such as over a day (e.g., $t_0$-$t_{20}$), the user 124 may use two or more different devices 1310-1340, such as to obtain the device-specific data sets over time, where each of the different devices determine an individual energy expenditure estimate 1410. In some cases, the user 124 may desire to view and/or review a total energy expenditure estimate, such as over a day.

In an illustrative synchronization example referring to FIG. 13, the user 124 may begin a day (e.g., duration $t_0$-$t_{20}$) by using a first device 1310 comprising at least one sensor configured to detect movements of the user. Upon use, the first device 1310 may communicate, or otherwise synchronize any accumulated data, such as for example, energy expenditure estimates determined by, for example, the second device 1320. The first device 1310 may then monitor activities performed by the user 124 over a first time a period (e.g., $t_1$-$t_4$) and determine a first energy expenditure estimate corresponding to the monitored activities. After computing the first energy expenditure estimate, the first device 1310, either manually or automatically, may synchronize the first energy expenditure estimate with at least the second device 1320. For example, a manual synchronization may be performed in response to a request (e.g., an input) received from the user 124. An automatic synchronization may be performed in response to one or more conditions determined by the apparatus 1310-1320 and/or communicated to the apparatus 1310-1320, such as an expiration of a repeating timer, a determined activity state, a determined time period, and/or one or more other conditions.

At a second time period (e.g., $t_4$-$t_6$), the user 124 may use the second device 1320 to monitor activities and determine a corresponding second energy expenditure estimate. After computing the second energy expenditure estimate, the second device 1320 may synchronize the second energy expenditure estimate with the first device 1310. Upon synchronization, the first device and/or the second device may be configured to determine and/or output a total energy expenditure estimate corresponding to the first energy expenditure estimate and the second energy expenditure estimate. In some cases, one or more of the first device and the second device may be configured to synchronize the determined total energy expenditure estimate. If differences are found between the synchronized values (e.g., due to accuracy differences, algorithm differences, etc.), one of the first device or the second device may be configured to modify or adjust the total energy expenditure estimate and to synchronize the modified total energy expenditure estimate between the devices 1310, 1320.

In some cases, two or more sensors of two or more devices 1310-1340 may obtain data from the user during the same absolute time period. In such cases, each device 1310-1340 may be configured to synchronize individual energy expenditure estimates determined by each device. In some cases, one or more of the devices may be configured to determine a combined energy expenditure estimate during the common time period based, at least in part, on the energy expenditure estimates of each synchronized device during the common time period, similarly to the illustrative example of FIG. 8, as discussed above. The combined energy expenditure estimate may be based on the accuracy in calculating energy expenditure for all of the available sensors or sensor systems. For example, metrics obtained using a first sensor of the first device 1310 may be combined with second metrics obtained from one or more of the devices 1320-1340 during a common time period (e.g., $t_2$-$t_4$). The metrics from the devices 1310-1340 may be combined using one or more algorithms based, at least in part, on a type of sensor used to collect the metrics, an accuracy of the sensor, an activity performed by the user 124, and the like. The selection of a particular sensor and/or device 1310-1320 and/or the accuracy of the sensors may be functions of the exercise that will be performed. For example, a first sensor may result in more accurate energy expenditure calculations while a user is running and a second sensor may result in more accurate energy expenditure calculations while a user is performing squats. In such cases, the combined energy expenditure estimate may be calculated using one or more of an average, a weighted average or a statistical solution to determine energy expenditure.

In some cases, such as during time period $t_{13}$-$t_{14}$, two or more of the devices 1310-1340 may be used to determine one or more metrics about athletic activity performed by the user 124. In some cases, the user 124 may determine which ones of the two or more devices 1310-1340 to use when monitoring any athletic activity, such as by specifying a device having the greatest accuracy for a particular metric. In other cases, the two or more devices 1310-1340 may be configured to determine, such as via a network (e.g., the BAN 1202, the LAN 1204, the WAN 1206) which of the devices 1310-1340 may have a greater accuracy associated with a metric associated with an athletic activity performed by the user. For example, the device 1310 may receive an indication from at least one other device (e.g., device 1330, 1340) that the at least one other device 1330, 1340 is being used to monitor athletic activity of the user 124. In some cases, the first device 1310 may broadcast an indication via the networks 1202-1206 that the first device 1310 is monitoring the athletic activity of the user 124. Next, the different devices 1310-1340 being used to monitor the same athletic activity of the user 124 may be configured to determine which one(s) of the devices 1310-1340 may be used to determine a metric (e.g., energy expenditure, blood pressure, force, heart rate, acceleration, velocity, etc.) associated with the athletic activity of the user 124. For example, a first device may be determined as having the greatest accuracy for a particular desired metric may be used to monitor that metric. In such cases, information about the metric may be synchronized with and/or used by the other devices 1320-1340, such as to determine an energy expenditure estimate of the user 124. In some cases, the metric may be synchronized between the different devices 1310-1340 at predetermined intervals (e.g., 4 seconds, 10 seconds, 30 seconds, etc.). In other cases, each of the devices 1310-1340 may each determine the particular metric, where the metric may be combined to determine a common metric over the monitored duration.

After determining the total energy expenditure estimate one or more devices, e.g. devices 1310-1340, may be configured to synchronize the total energy expenditure estimate over one or more of the BAN 1202, the LAN 1204 and/or the WAN 1206. In some cases, a device, such as the first device 1310 may be configured to be a master of the system and the other devices 1320-1340 may be configured as slaves. For example, the first device 1310 may receive the energy expenditure estimates from one or more other devices 1320-1340 to determine the total energy expenditure estimate and then synchronize the total energy expenditure estimate with the other devices 1320-1340 on the network.

When computing the total energy expenditure estimates, the devices 1310-1340 may be configured to display and/or manage the energy expenditure information using two or more different methods. For example, a device 1400 may be configured to determine a total energy estimate from two or more different energy expenditure estimates synchronized over a network (e.g., BAN 1202, LAN 1204, WAN 1206). For example, the device 1410 may be configured to determine a local energy expenditure estimate 1410, and to synchronize the local energy expenditure estimate 1410 with one or more different energy expenditure estimates 1415 synchronized over the network via a communication interface 1420. In some cases, the synchronized energy expenditure estimates 1415 may be combined (e.g., summed) using one or more computation modules 1425 to determine the total energy expenditure estimate 1430. In some cases, the total energy expenditure estimate 1430 may be computed by the computation module 1425 using one or more algorithms, weighting factors, or the like.

Once computed, the total energy expenditure estimate 1430 may be used as a baseline energy expenditure estimate. In one embodiment, the baseline energy expenditure estimate may then be used to overwrite the local energy expenditure estimate 1410, such that any further energy expenditure estimate determined by the device 1450 is added to the new baseline value. The new baseline value may then be synchronized between the different devices on the network via the communication interface 1420. In some cases, the device 1410 may include a display 1440 that may be utilized to display one or more of the local energy expenditure estimate 1410, the synchronized energy expenditure estimate 1414 and/or the total energy expenditure estimate 1430. In some cases, the display may be configured to display an indication of a synchronization status of the network.

In some cases, the apparatus 1450 may be configured to determine the local energy expenditure estimate 1460. The communication interface 1420 may be configured to synchronize two or more energy expenditure estimates between the device 1450 and one or more different devices. For example, the energy expenditure estimates may be stored in different memory areas, such as in the system memory 108, of the device 1450. A first energy expenditure estimate 1462 received from a first device may be stored in a first memory area, a second energy expenditure estimate 1464 received from a second device 1330 may be stored in a second memory area, and so on. In some cases, the different energy expenditure estimates 1460-1464 stored in the system memory 108 may be used to determine the total energy expenditure estimate. For example, the device 1450 may use the different energy expenditure estimates as an offset which may be added to the local energy expenditure estimate 1460. In some cases, the two or more of the different energy expenditure estimates 1460-1464 may be combined to determine a time interval common to the first energy expenditure estimate and the second energy expenditure estimates 1464 and combine the energy expenditure estimates associated with the common time period to determine a third energy expenditure estimate corresponding to an exercise performed by the user 124. In some cases, the device 1450 may be configured to determine a total energy estimate by combining (e.g., summing, applying weighting factors, applying an algorithm, etc.) using the computation module 1425. The computation module may store the total energy expenditure estimate 1480. In some cases, the display 1440 may be configured to present, to the user 124, one or more of the local energy expenditure estimate 1460, the energy expenditure estimates of the two or more different devices 1462-1464 and/or the total energy expenditure estimate 1480.

Figure 15:
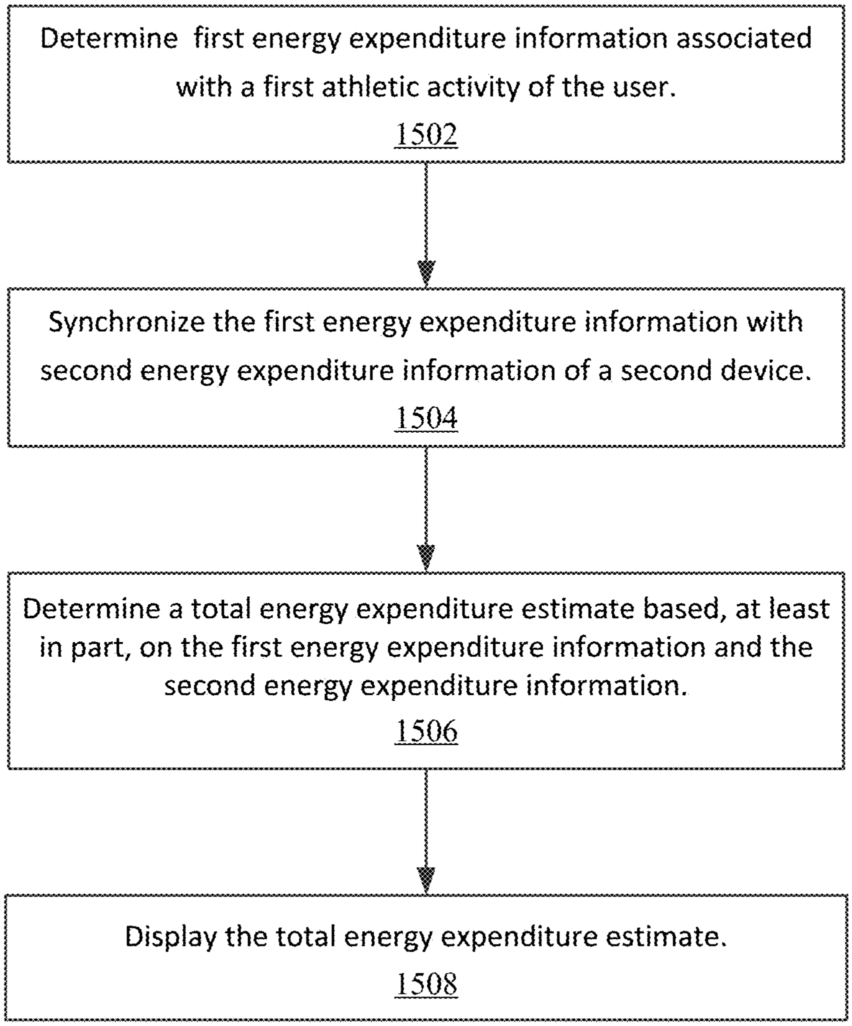
FIG. 15 illustrates an example flow diagram of a method for calculating a combined energy expenditure estimate for a user based on energy expenditure estimates obtained by two or more different devices.

FIG. 15 illustrates an example flow diagram 1500 of a method for calculating a combined energy expenditure estimate for a user 124 based on energy expenditure estimates obtained by two or more different devices 1310-1340. The method may be implemented by a computer, such as, for example, computer 102, device 138, 140 and/or 142, as well as or other apparatuses 1211-1214, 1222-1228, and/or 1310-1340. The blocks shown in FIG. 15 may be rearranged, some blocks may be removed, additional blocks may be added, each block may be repeated one or more times, and the flow diagram may be repeated one or more times. At 1502, the processor 106 of a first device 1310 may be configured to determine first energy expenditure information associated with a first athletic activity performed by the user 124. In some cases, the first energy expenditure information may include a first energy expenditure estimate and one or more different time stamps, such as first time stamp associated with a start of a first athletic activity and/or a second time stamp associated with an end of the first athletic activity. In some cases, the second device 1320 may determine the second energy expenditure information associated with a second athletic activity of the user. The second energy expenditure information may include a second energy expenditure estimate and at least one second time stamp associated with the second athletic activity. At 1504, the first device 1310 may synchronize the first energy expenditure information with second energy expenditure information of a second device (e.g., one or more of the devices 1320-1340), such as over a network (e.g., the BAN 1202, the LAN 1204, and/or the WAN 1206).

At 1506, the first device 1310 may determine, such as by using the processor 108, a total energy expenditure estimate based, at least in part, on the first energy expenditure information and the second energy expenditure information. At 1508, the first device may display at least the total energy expenditure estimate, such as to the user 124. In some cases, the first device 1310 and/or the second device 1320 may determine a different energy expenditure estimate used by the first device 1310, such as by overwriting at least one of the first energy expenditure estimate and the second energy expenditure estimate with the total energy expenditure estimate. In some cases, the first device may determine the total energy expenditure estimate as a combination of a first offset associated with the first energy expenditure estimate and a second offset associated with the second energy expenditure estimate. The display may display the total energy expenditure estimate as a combination of at least the first offset and/or the second offset. In some cases, the display may display energy expenditure information for the first device 1310 and/or one or more of the different devices 1320-1340 after synchronizing the energy expenditure information.

Figure 16:
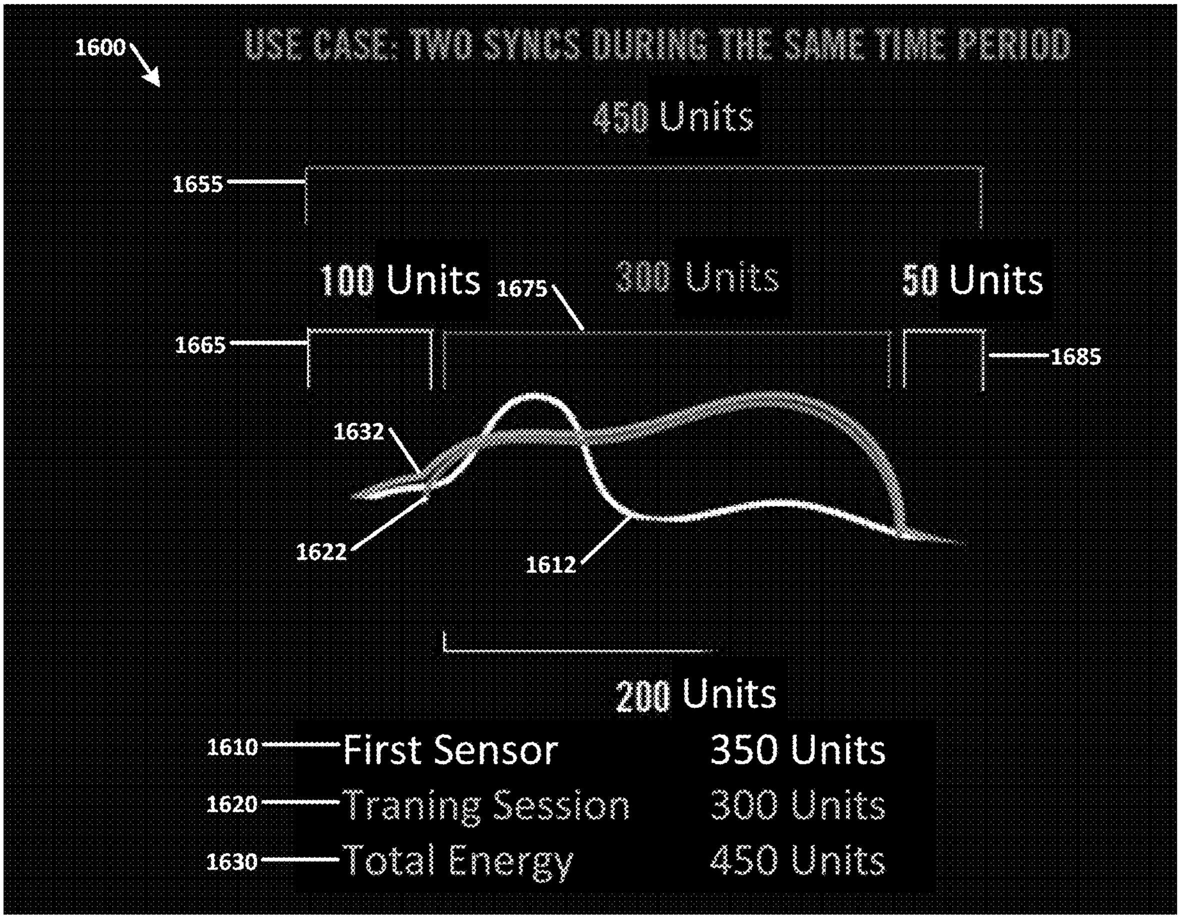
FIG. 16 shows an illustrative chart showing use of two devices capable of monitoring energy expenditure of a user while performing one or more athletic activities and/or exercises over a common time interval.

FIG. 16 shows an illustrative chart showing use of two devices capable of monitoring energy expenditure of a user while performing one or more athletic activities and/or exercises over a common time interval. For example, a user may perform one or more athletic activities (e.g., running, biking, daily activities, etc.) over a time interval. As discussed herein, multiple sensors or devices may monitor or otherwise sense (actively or passively) the user's activities. As such, parameters relating to the user's activity may be captured using sensors, which may be located on one or more devices. The sensors may monitor the user's motion, physiological properties, and/or other parameters. As discussed above, a first sensor may result in more accurate determinations, such as for example, energy expenditure calculations while a user is running and a second sensor may result in more accurate determinations, e.g., energy expenditure calculations, while a user is performing squats. Although the following examples (as well as other examples disclosed herein) provide examples with reference to energy expenditure, these are merely examples and not intended to limit the scope of this disclosure. In instances where data regarding certain parameters, such as energy expenditure, are obtained from two or more sensors or determined by different mathematical calculations, certain aspects of this disclosure may be implemented to determine a resultant output. In such cases, the combined energy expenditure estimate may be calculated using one or more of an average, a weighted average or a statistical solution. However, such calculations may not be practical in every situation. As such, another method of combining energy expenditure information gathered using different devices may be desired.

For example, in some cases, a user may perform athletic activities using sensors provided by two or more vendors. As such, a simple set of easily understandable rules for combining energy expenditure information may be desirable. Such rules may be applied in a common manner across all users and/or for devices provided by multiple vendors. The rules may include ensuring that a user's recorded total energy expenditures will never decrease and that information gathered during one or more sessions of athletic activity will be preserved. In such cases, the energy expenditure information may always be available and/or accessible to a user via an application, whether or not the energy expenditure information is directly reflected in the total energy expenditure information.

In certain implementations, a device, such as the device 1400, 1450 may determine whether energy expenditure information received from at least two devices overlap over one or more time intervals. Certain embodiments may determine whether a minimum threshold of an interval is met. For example, if a second device or sensor only intermittently provides data, it may not meet a threshold requirement for further analysis. Intervals may be any time unit, including fractions of a second, seconds, minutes, hours, days, etc. and derivatives thereof. If two or more sensors or device gather information or for a threshold amount of information, If so, energy expenditure information from the device which recorded the most energy expenditures over a particular time interval may be used. The determination of "most" or highest may be unit dependent, such as highest peak value during any unit of time within the time interval, the highest cumulative values, the highest average value over the overlapping collection period, among others. The determination of which parameters or values to use may be made by device 1400, 1450.

Unlike other methods discussed herein, the energy expenditure information may not be combined. Rather, the device 1400, 1450 may determine one or more time intervals during which energy expenditure information overlap for two or more sensors/devices recording the user's athletic activities, as shown in FIG. 16. Here, energy expenditure information may be received over a first time period 1655. During this time a user may perform one or more athletic activities and use one or more sensors for monitoring the activity. The chart 1600 shows an illustrative example of a user participating in an athletic activity over the time period 1655. Here, the user may use a first sensor 1610 (e.g., a wrist worn sensor) to provide a first energy expenditure estimate 1612 over the time period 1655 and a second sensor 1620 (e.g., a camera) to provide a different second energy expenditure estimate 1622 over at least a portion of the same time period 1655. Or perhaps, the user has a mobile device, e.g., mobile telephone or tablet in their pocket or being carried that measures movements. Thus, while the mobile device in the pocket or bag may be less accurate in some embodiments due to capturing less motion, it will serve as a fall back device for when the more accurate device is not available, such as by the battery dying or the user removing it from their wrist. The device 1400, 1450 may be configured to receive the first and second energy expenditure estimates 1612, 1622 from the first device 1610 and the second device 1620 and to combine this energy expenditure information into a total energy expenditure estimation 1630 over the time period 1655, as shown in the chart at 1632.

To generate the total energy expenditure estimation 1630, the device 1450, 1455 may receive, such as via a synchronization process, the energy expenditure information from the first sensor 1610 and the second sensor 1620 via a communication link (e.g., a wireless communication link, a wired communication link, and/or combinations thereof). The first energy expenditure estimate 1612 and the second energy expenditure estimate 1622 may be analyzed over the time period 1655 to determine one or more sub-time periods 1665, 1675, 1685, where the energy expenditure estimates 1612, 1622 provided by first sensor 1610 and the second sensor 1620 overlap (which may be subjected to threshold requirements). During this analysis, the device 1400, 1450 may determine each sub-time period 1665, 1675, 1685 based on which of the sensors 1610, 1620 has provided the greater or larger amount of energy expenditure information 1612, 1622 during that particular time period. For example, over the first sub-time period 1665 and the third sub-time period 1685, the first sensor 1610 has provided the most energy expenditure information over those time intervals and during the second sub-time interval 1675, the second sensor 1620 has provided the greater amount of energy expenditure information. In this case, the determination is based upon the largest accumulation of energy expenditure units during the overlapping period, however, as discussed above, other determinations are within the scope of this disclosure. In some cases, two or more sensors may be used over the complete time interval 1655. In other cases, one or more sensors may be used over a portion of the complete time interval 1655, as shown in the illustrative example of chart 1600. Here, the second sensor 1620 may have been used primarily during the second sub-time interval 1665.

To determine the total energy expenditure estimate 1632, the device 1400, 1450 may process the first and second energy expenditure estimates 1612, 1622 using an energy expenditure calculation module, which may comprise hardware and software. For example, the device 1400, 1450 may determine the total energy expenditure estimate 1632 based on which sensor 1610, 1620 provides a greater of energy expenditure estimate over a particular sub-time period 1655, 1675, 1685. As can be seen in the chart 1600, the first sensor provides a greater amount of energy expenditure information over the first and third time intervals 1665, 1685, 100 units of energy expenditure information and 50 units, respectively. Over the second time period 1675, the second sensor 1620 provides the greater cumulative amount of energy expenditure information (e.g., 300 units vs. 200 units). As such, total energy expenditure estimate 1632 corresponds primarily to the first energy expenditure estimate 1612 over the first and third sub-time intervals 1665, 1685, and to the second energy expenditure estimate 1622 over the second sub-time interval 1675. This may be advantageous in implementations in which a mobile device is routinely available as a fall back device, however, data from the more specialized device may be used when available. In some cases, the device 1400, 1450 may smooth the total energy expenditure estimate 1632 at the transition between time intervals (e.g., between the first sub-time interval 1665 and the second sub-time interval 1675 and between the second sub-time interval 1675 and the third sub-time interval 1685). Those skilled in the art will appreciate that the illustrative algorithm used to process the energy expenditure information received from the different sensors over a common time period is illustrative and other such algorithms for combining the energy expenditure information may be used, such as by using an average, using one or more weighting factors, adding a difference, and the like.

Figure 17:
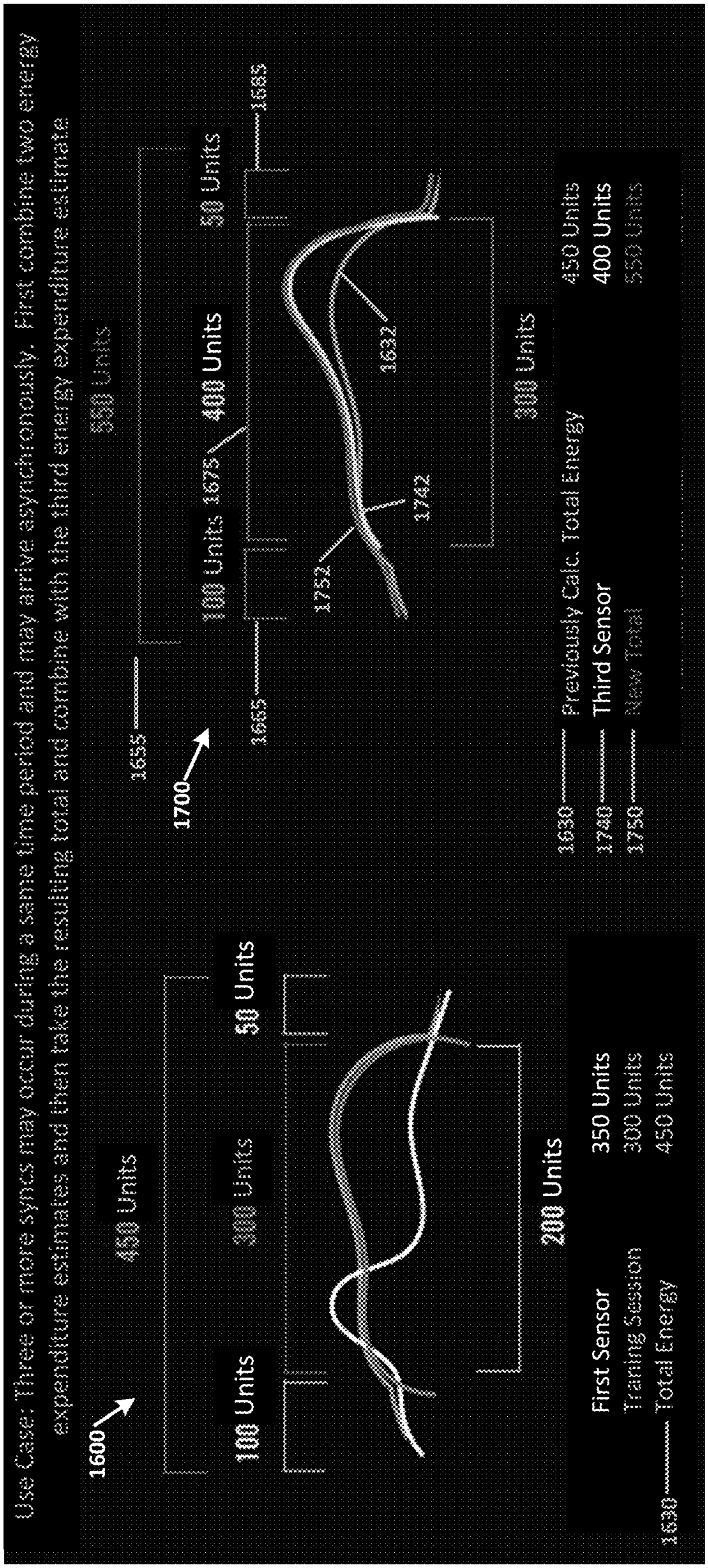
FIG. 17 shows an illustrative charts showing use of two devices capable of monitoring energy expenditure of a user while performing one or more athletic activities and/or exercises over a common time interval.

FIG. 17 shows illustrative chart 1600 (replicated on a smaller scale from FIG. 16) and chart 1700 showing use of three or more devices 1610, 1620, 1740 capable of monitoring energy expenditure of a user while performing one or more athletic activities and/or exercises over a common time interval 1655. In the illustrative use case shown in FIG. 17, three devices 1610, 1620, 1730 may be used to monitor athletic activity of the user over the common time interval 1685. For example, the user may use a wrist-worn sensor, a camera and an acceleration sensor. In some cases, one or more of the sensors 1610, 1620, 1740 may communicate with a software application that may process raw sensor data to calculate energy expenditure information subsequently provided to the device 1400, 1450. In some cases, the energy expenditure information 1612, 1622, and 1742 may be communicated to the device 1400, 1450 for processing via a communication link, such as by asynchronously synchronizing the sensors to the device. In some cases, the sensor information may be synchronously communicated to the device 1400, 1450.

Once the energy expenditure estimates 1612, 1622, 1742 have been received, the device 1400, 1450 may process the energy expenditure estimates 1612, 1622, 1742, e.g., using computer-executed instructions stored on a non-transitory computer-readable medium. to generate a total energy expenditure estimate 1752 of the user during the time interval 1655. In an illustrative example, the device may first process the energy expenditure information received from the first and second devices to produce a total energy expenditure estimate 1632, as discussed above in reference to FIG. 16. Once calculated, the device 1400, 1450 may then combine the energy expenditure estimate 1742 with the total energy expenditure estimate 1632 to provide a new total energy expenditure estimate 1752 corresponding to the combined energy expenditure information received from the sensors 1610, 1620, and 1740. The new energy expenditure information may be determined by comparing the total energy expenditure estimate 1632 with the third energy expenditure estimate 1742 over the different sub-time intervals 1665, 1675 and 1685. As before, for a particular sub-time interval, the new total energy expenditure estimate 1752 may correspond to the energy expenditure estimate 1632, 1742 having the greater value over each particular sub-time interval 1665, 1677, 1685. As can be seen from the illustrative chart 1700, the new total energy estimate 1752 corresponds to the previous total energy expenditure 1632 estimate over the first and third time intervals 1665, 1685 and with the third energy expenditure estimate 1742 over the second time interval 1675. In some cases, the new total energy expenditure estimate 1752 may be smoothed at the transition between the first sub-time interval and the second sub-time interval and between the second sub-time interval and the third sub-time interval.

In some cases, one or more sensors may synchronize with different devices to compute a total energy expenditure estimate. Each of the different devices may separately compute a total energy expenditure estimate based on the devices synchronized. In some cases, the devices may further synchronize the energy expenditure information. In other cases, each device may individually aggregate energy expenditure information. For example, a user may use sensors from two or more different vendors, where a first set of sensors may be configured to synchronize energy expenditure information with a first device and a second set of sensors may be configured to synchronize energy expenditure information with a second device. In such cases, the energy expenditure information may be totaled separately on the different devices. For example, the first device may store a total energy expenditure estimate of 5000 units gathered using the first set of sensors and the second device may store a total energy expenditure estimate of 6000 units gathered using the second set of sensors.

Conclusion

Providing an activity environment having one or more of the features described herein may provide a user with an immersive experience that will encourage and motivate the user to engage in athletic activities and improve his or her fitness. Users may further communicate through social communities and challenge one another to reach various levels of fitness, and to view their fitness level and activity.

The transmission of information between devices ensures that users are provided with energy expenditure information, regardless of which device they are currently using. Moreover, the energy expenditure information can be collated to provide accurate combined energy expenditure for the user which takes into account the devices used by the user and any overlap in their use. This may enable the user to use devices which are specifically adapted to one or more activities while still retaining an overview of their energy expenditure. Accordingly, devices may be tailored more specifically to certain activities. On the other hand, the system can be setup as a master and slave arrangement which may allow slave devices to have a reduced functionality, which in turn may reduce their complexity, cost, and/or size, without any significant disadvantage for the user. In addition, the communication of information between devices potentially reduces data transmission, processing and storage burdens.

Aspects of the embodiments have been described in terms of illustrative embodiments thereof. Numerous other embodiments, modifications and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

In any of the above aspects, the various features may be implemented in hardware, or as software modules running on one or more processors. Features of one aspect may be applied to any of the other aspects.

There may also be provided a computer program or a computer program product for carrying out any of the methods described herein, and a computer readable medium having stored thereon a program for carrying out any of the methods described herein. A computer program may be stored on a computer-readable medium, or it could, for example, be in the form of a signal such as a downloadable data signal provided from an Internet website, or it could be in any other form.

For the avoidance of doubt, the present application extends to the subject-matter described in the following numbered paragraphs (referred to as "Para" or "Paras"):

Para 1. An apparatus for use with a user performing an exercise comprising:

at least one processor;

a first sensor configured to monitor a first exercise performed by the user;

a communication circuit configured to communicate at least energy expenditure information between the apparatus and at least a second device, the energy expenditure information including at least a first energy expenditure estimate corresponding to the first exercise monitored by the first sensor and a second energy expenditure estimate corresponding to a second exercise monitored by at least the second device;

at least one tangible memory storing computer-executable instructions that, when executed by the at least one processor, cause the apparatus at least to:

monitor, with the sensor, the first exercise performed by the user;

determine, by the at least one processor, the first energy expenditure estimate of the user corresponding to the monitored first exercise;

communicate, by the communication circuit, energy expenditure information between the apparatus and at least the second device, the energy expenditure information including the first energy expenditure estimate and the second energy expenditure estimate; and determine, by the at least one processor, a combined energy expenditure estimate of the user based, at least in part, on the first energy expenditure estimate and the second energy expenditure estimate.

Para 2. The apparatus of Para 1, comprising a display for displaying at least the combined energy expenditure estimate of the user.

Para 3. The apparatus of Para 1 or 2, wherein the at least one tangible memory stores further computer-executable instructions that, when executed by the at least one processor, cause the apparatus at least to communicate the energy expenditure information between the apparatus and at least the second device after expiration of a specified time interval.

Para 4. The apparatus of any preceding Para, wherein the at least one tangible memory stores further computer-executable instructions that, when executed by the at least one processor, cause the apparatus at least to communicate the combined energy expenditure estimate between the apparatus and at least the second device.

Para 5. The apparatus of any preceding Para, wherein the at least one tangible memory stores further computer-executable instructions that, when executed by the at least one processor, cause the apparatus at least to communicate the energy expenditure information between the apparatus and at least the second device in response to a synchronization request from the user.

Para 6. The apparatus of any preceding Para, wherein the at least one tangible memory stores further computer-executable instructions that, when executed by the at least one processor, cause the apparatus at least to automatically communicate the energy expenditure information between the apparatus and at least the second device after determining a completion of at least one of the first athletic activity and the second athletic activity.

Para 7. The apparatus of any preceding Para, wherein the energy expenditure information includes at least one of at least one time stamp associated with the energy expenditure estimate, an activity type, and a system clock time.

Para 8. The apparatus of any preceding Para, wherein the at least one tangible memory stores further computer-executable instructions that, when executed by the at least one processor, cause the apparatus at least to synchronize a system clock of the apparatus with a system clock of the second device.

Para 9. The apparatus of any preceding Para, wherein the at least one tangible memory stores further computer-executable instructions that, when executed by the at least one processor, cause the apparatus at least to:

determine a common time interval associated with both the first athletic activity and the second athletic activity; and determine a third energy expenditure estimate associated with the combined first athletic activity and the second athletic activity during the common time interval, and determine the combined energy expenditure estimate based, at least in part, on the third energy expenditure estimate.

Para 10. The apparatus of any preceding para, wherein the at least one tangible memory stores further computer-executable instructions that, when executed by the at least one processor, cause the apparatus at least to:

determine a common time interval associated with the first energy expenditure estimate and the second energy expenditure estimate, determine, for the common time interval, whether the first energy expenditure estimate is greater than the second energy expenditure estimate, wherein:

when the first energy expenditure estimate is greater than the second energy expenditure estimate, set the combined energy expenditure estimate for the common time interval to the first energy expenditure estimate; and when the first energy expenditure estimate is not greater than the second energy expenditure estimate, set the combined energy expenditure estimate over the common time interval equal to the second energy expenditure estimate.

Para 11. A system comprising:

a first monitoring device configured to determine a first energy expenditure estimate associated with athletic activity performed by a user over a first duration;

a second device, in communication with the first monitoring device, the second device configured to store at least a second energy expenditure estimate associated with athletic activity performed by the same user over a second duration; and wherein the first monitoring device includes:

a first processor;

a first tangible memory device storing computer-executable instructions that, when executed by the first processor, cause the first monitoring device at least to:

send, via the communications network, the first energy expenditure estimate to the second device;

receive, via a communications network, the second energy expenditure estimate from the second device; and determine, by the processor, a total energy expenditure estimate based, at least in part, on the first energy expenditure estimate and the second energy expenditure estimate; and a display to display the total energy expenditure estimate to the user.

Para 12. The system of Para 11, wherein the second device comprises:

a second processor;

a second tangible memory device storing computer-executable instructions that, when executed by the second processor, cause the second device at least to:

receive, via a communications network, the first energy expenditure estimate from the first monitoring device;

send, via the communications network, the second energy expenditure estimate to the first monitoring device; and determine, by the second processor, a total energy expenditure estimate based, at least in part, on the first energy expenditure estimate and the second energy expenditure estimate; and a second display for displaying the total energy expenditure estimate to the user.

Para 13. The system of any of Paras 11 or 12, wherein the second device comprises:

a sensor configured to monitor an athletic activity performed by the user; and wherein the second tangible memory stores further executable instructions that, when executed by the second processor, cause the second device to at least determine the second energy expenditure estimate based, at least in part, on information obtained by the sensor.

Para 14. The system of any of Paras 11 to 13, wherein the first tangible memory stores further computer-executable instructions that, when executed by the first processor, cause the first monitoring device at least to synchronize, via the communications network, the total energy expenditure estimate determined by the first monitoring device with the second device.

Para 15. The system of any of Paras 11 to 14, wherein the first tangible memory stores further computer-executable instructions that, when executed by the first processor, cause the first monitoring device at least to determine the total energy expenditure estimate as a sum of at least a portion of the first energy expenditure estimate and at least a portion of the second energy expenditure estimate.

Para 16. The system of any of Paras 11 to 15, wherein the first tangible memory stores further computer-executable instructions that, when executed by the first processor, cause the first monitoring device at least to:

determine an exercise performed by the user during a time period common to the first duration and the second duration, determine a third energy expenditure estimate corresponding to the exercise performed during the common time period; and wherein the total energy expenditure estimate further includes the third energy expenditure estimate.

Para 17. The system of any of Paras 11 to 16, wherein the first tangible memory stores further computer-executable instructions that, when executed by the first processor, cause the first monitoring device at least to:

synchronize a first system clock associated with the first monitoring device with a second system clock associated with the second monitoring device, and adjust one or more time stamps associated with the first energy expenditure estimate based on a difference between the first system clock and the second system clock.

Para 18. The system of any of Paras 10 to 17, wherein the first tangible memory stores further computer-executable instructions that, when executed by the first processor, cause the first monitoring device at least to overwrite the first energy expenditure estimate with total energy expenditure estimate.

Para 19. The system of any of Paras 11 to 18, wherein the first tangible memory stores further computer-executable instructions that, when executed by the first processor, cause the first monitoring device at least to:

determine an offset corresponding to at least a portion of the second energy expenditure estimate; and display the total energy expenditure estimate as a sum of the first energy expenditure estimate and the offset.

Para 20. A method comprising:

determining, by a first processor of a first device, first energy expenditure information associated with a first athletic activity of the user, the first energy expenditure information including a first energy expenditure estimate and a first time stamp associated with the first athletic activity;

synchronizing, via a network, the first energy expenditure information with second energy expenditure information of a second device;

determining, by the processor of the first device, a total energy expenditure estimate based, at least in part, on the first energy expenditure information and the second energy expenditure information; and displaying, on a display device, the total energy expenditure estimate.

Para 21. The method of Para 20, further comprising:

overwriting at least one of the first energy expenditure estimate and the second energy expenditure estimate with the total energy expenditure estimate.

Para 22. The method of Para 20 or 21, further comprising determining, by the first processor, the total energy expenditure estimate as a combination of a first offset associated with the first energy expenditure estimate and a second offset associated with the second energy expenditure estimate; and displaying, on the display device, the total energy expenditure estimate and at least one of the first offset and the second offset.

Para 23. The method of any of Paras 20 to 22 further comprising determining, by a second processor of the second device, second energy expenditure information associated with a second athletic activity of the user, the second energy expenditure information including a second energy expenditure estimate and a second time stamp associated with the second athletic activity.

Para 24. A non-transitory computer-readable medium comprising executable instructions that when executed cause a computer device to perform the method as described in any of Paras 20 to 23.

Para 25. The method of any of Paras 20 to 24 further comprising:

determining a common time interval associated with the first energy expenditure estimate and the second energy expenditure estimate, determining, for the common time interval, whether the first energy expenditure estimate is greater than the second energy expenditure estimate, wherein:

when the first energy expenditure estimate is greater than the second energy expenditure estimate, setting the combined energy expenditure estimate for the common time interval to the first energy expenditure estimate; and when the first energy expenditure estimate is not greater than the second energy expenditure estimate, setting the combined energy expenditure estimate over the common time interval equal to the second energy expenditure estimate.

We claim:

1. An apparatus comprising:

at least one processor; and at least one tangible memory storing computer-executable instructions that, when executed by the at least one processor, cause the apparatus at least to:

monitor, with a sensor, movements performed by a user of a plurality of users, the sensor comprises an oxygen sensor or a force sensor and an oxygen sensor;

receive, from an imaging device, an image of the movements performed by the user;

identify, based on the image, first repetitions of a first user movement during the movements performed by the user;

identify, based on a first repetition of the first user movement of the first repetitions of the first user movement, a first exercise;

determine, by the at least one processor and while the user is performing the repetitions of the first user movement, a first energy expenditure estimate of the user corresponding to the first repetition of the first user movement;

receive, from a second computing device, a second energy expenditure estimate of a second user of the plurality of users; and display, via a user interface, a ranking of the plurality of users based on a comparison of the first energy expenditure estimate and the second energy expenditure estimate, wherein the ranking displays each user's energy expenditure as a percentage of a user-specific ideal expenditure value associated with an exercise, and wherein a first user, whose energy expenditure exceeds 100% of a first user-specific ideal expenditure value associated with the first user, is ranked lower than a second user whose energy expenditure is closer to 100% of a second user-specific ideal expenditure value associated with the second user.

2. The apparatus of claim 1, wherein the computer-executable instructions further cause the apparatus to:

calculate, based on the image, an adjustment factor based on a user's form when performing the first repetition of the first user movement; and determine, by the at least one processor, a first adjusted energy expenditure estimate of the user for the first repetition of the first user movement based on the first energy expenditure estimate and the adjustment factor.

3. The apparatus of claim 2, wherein the computer-executable instructions further cause the apparatus to:

determine, by the at least one processor and while the user is performing the repetitions of the first user movement, a third energy expenditure estimate of the user corresponding to a second repetition of the first user movement;

calculate, based on the image, a second adjustment factor based on the user's form when performing the second repetition of the first user movement; and determine, by the at least one processor, a second adjusted energy expenditure estimate of the user for the second repetition of the first user movement based on the third energy expenditure estimate and the second adjustment factor.

4. The apparatus of claim 3, wherein the computer-executable instructions further cause the apparatus to:

determine, by the at least one processor based on the first adjusted energy expenditure estimate and the second adjusted energy expenditure estimate, a first combined energy expenditure estimate of the user for the first exercise.

5. The apparatus of claim 1, wherein the ranking of the plurality of users is displayed as a percentage of an ideal expenditure value associated with an exercise.

6. The apparatus of claim 5, wherein the ranking of the plurality of users is displayed as a percentage of an ideal expenditure value associated with an exercise, wherein a first ideal expenditure value of the first user is different than a second ideal expenditure value of the second user.

7. The apparatus of claim 6, wherein identification that the second energy expenditure estimate is greater than the second ideal expenditure value, the second user is ranked lower than the first user.

8. The apparatus of claim 1, wherein the computer-executable instructions further cause the apparatus to:

identify, based on the image, repetitions of a second user movement during the movements performed by the user;

identify, based on a first repetition of the second user movement of the repetitions of the second user movement, a second exercise;

determine, by the at least one processor and while the user is performing the repetitions of the second user movement, a third energy expenditure estimate of the user corresponding to the first repetition of the second user movement;

calculate, based on the image, a third adjustment factor based on the user's form when performing the first repetition of the second user movement; and determine, by the at least one processor, a third adjusted energy expenditure estimate of the user for the first repetition of the second user movement based on the third energy expenditure estimate and the third adjustment factor.

9. The apparatus of claim 8, wherein the computer-executable instructions further cause the apparatus to:

determine, by the at least one processor and while the user is performing the repetitions of the second user movement, a fourth energy expenditure estimate of the user corresponding to a second repetition of the second user movement;

calculate, based on the image, a second adjustment factor based on the user's form when performing the second repetition of the user movement; and determine, by the at least one processor, a fourth adjusted energy expenditure estimate of the user for the second repetition of the second user movement based on the third energy expenditure estimate and the third adjustment factor.

10. A system comprising:

a sensor configured to monitor an exercise performed by a user, wherein the sensor is located on a body of the user and wherein the sensor comprises one of an oxygen sensor or a force sensor and an oxygen sensor; and a computing device comprising:

at least one processor; and at least one tangible memory storing computer-executable instructions that, when executed by the at least one processor, cause the computing device at least to:

monitor, with the sensor, movements performed by a first user of a plurality of users;

receive, from an imaging device, an image of the movements performed by the user;

identify, based on the image, first repetitions of a first user movement during the movements performed by the user;

identify, based on a first repetition of the first user movement of the first repetitions of the first user movement, a first exercise;

determine, by the at least one processor and while the user is performing the repetitions of the first user movement, a first energy expenditure estimate of the user corresponding to the first repetition of the first user movement;

receive, from a second computing device, a second energy expenditure estimate of a second user of the plurality of users; and display, via a user interface, a ranking of the plurality of users based on a comparison of the first energy expenditure estimate and the second energy expenditure estimate, wherein the ranking displays each user's energy expenditure as a percentage of a user-specific ideal expenditure value associated with an exercise, and wherein a first user, whose energy expenditure exceeds 100% of a first user-specific ideal expenditure value associated with the first user, is ranked lower than a second user whose energy expenditure is closer to 100% of a second user-specific ideal expenditure value associated with the second user.

11. The system of claim 10, wherein the computer-executable instructions further cause the computing device to:

calculate, based on the image, an adjustment factor based on a user's form when performing the first repetition of the first user movement; and determine, by the at least one processor, a first adjusted energy expenditure estimate of the user for the first repetition of the first user movement based on the first energy expenditure estimate and the adjustment factor.

12. The system of claim 10, wherein the computer-executable instructions further cause the computing device to:

determine, by the at least one processor and while the user is performing the repetitions of the first user movement, a third energy expenditure estimate of the user corresponding to a second repetition of the first user movement;

calculate, based on the image, a second adjustment factor based on the user's form when performing the second repetition of the first user movement; and determine, by the at least one processor, a second adjusted energy expenditure estimate of the user for the second repetition of the first user movement based on the third energy expenditure estimate and the second adjustment factor.

13. The system of claim 11, wherein the computer-executable instructions further cause the computing device to:

determine, by the at least one processor based on the first adjusted energy expenditure estimate and the second adjusted energy expenditure estimate, a first combined energy expenditure estimate of the user for the first exercise.

14. The system of claim 10, wherein the computer-executable instructions further cause the computing device to:

identify, based on the image, repetitions of a second user movement during the movements performed by the user;

identify, based on a first repetition of the second user movement of the repetitions of the second user movement, a second exercise;

determine, by the at least one processor and while the user is performing the repetitions of the second user movement, a third energy expenditure estimate of the user corresponding to the first repetition of the second user movement;

calculate, based on the image, a third adjustment factor based on the user's form when performing the first repetition of the second user movement; and determine, by the at least one processor, a third adjusted energy expenditure estimate of the user for the first repetition of the second user movement based on the third energy expenditure estimate and the third adjustment factor.

15. The system of claim 10, wherein the ranking of the plurality of users is displayed as a percentage of an ideal expenditure value associated with an exercise.

16. The system of claim 15, wherein the ranking of the plurality of users is displayed as a percentage of an ideal expenditure value associated with an exercise, wherein a first ideal expenditure value of the first user is different than a second ideal expenditure value of the second user.

17. The system of claim 16, wherein identification that the second energy expenditure estimate is greater than the second ideal expenditure value, the second user is ranked lower than the first user.

18. A method comprising:

monitoring, with a sensor, movements performed by a first user of a plurality of users, wherein the sensor comprises one of an oxygen sensor or a force sensor and an oxygen sensor;

receiving, by a computing device from an imaging device, an image of the movements performed by the first user;

identifying, by the computing device based on the image, first repetitions of a first user movement during the movements performed by the first user;

identifying, by the computing device based on a first repetition of the first user movement of the first repetitions of the first user movement, a first exercise;

determining, by the computing device and while the first user is performing the repetitions of the first user movement, a first energy expenditure estimate of the first user corresponding to the first repetition of the first user movement;

receiving, from a second computing device, a second energy expenditure estimate of a second user of the plurality of users; and displaying, via a user interface, a ranking of the plurality of users based on a comparison of the first energy expenditure estimate and the second energy expenditure estimate, wherein the ranking displays each user's energy expenditure as a percentage of a user-specific ideal expenditure value associated with an exercise, and wherein a first user, whose energy expenditure exceeds 100% of a first user-specific ideal expenditure value associated with the first user, is ranked lower than a second user whose energy expenditure is closer to 100% of a second user-specific ideal expenditure value associated with the second user.

19. The method of claim 18 further comprising:

calculating, by the computing device based on the image, an adjustment factor based on a user's form when performing the first repetition of the first user movement; and determining, by the computing device based on the first energy expenditure estimate and the adjustment factor, a first adjusted energy expenditure estimate of the user for the first repetition of the first user movement; and displaying, on a display device, the first adjusted energy expenditure estimate.

20. The method of claim 18, wherein the ranking of the plurality of users is displayed as a percentage of an ideal expenditure value associated with an exercise.

* * * * *